US010696951B2

(12) United States Patent
Uemura et al.

(10) Patent No.: US 10,696,951 B2
(45) Date of Patent: Jun. 30, 2020

(54) METHOD FOR CULTURING PLURIPOTENT STEM CELLS

(71) Applicant: JTEC Corporation, Ibaraki-shi, Osaka (JP)

(72) Inventors: Toshimasa Uemura, Suita (JP); Yui Onomura, Tsukuba (JP); Takashi Tsumura, Ibaraki (JP)

(73) Assignee: JTEC Corporation, Osaka (JP)

( * ) Notice: Subject to any disclaimer, the term of this patent is extended or adjusted under 35 U.S.C. 154(b) by 0 days.

(21) Appl. No.: 15/515,449

(22) PCT Filed: Sep. 30, 2015

(86) PCT No.: PCT/JP2015/077824
§ 371 (c)(1),
(2) Date: Mar. 29, 2017

(87) PCT Pub. No.: WO2016/052657
PCT Pub. Date: Apr. 7, 2016

(65) Prior Publication Data
US 2017/0218343 A1    Aug. 3, 2017

(30) Foreign Application Priority Data
Sep. 30, 2014  (JP) ................ 2014-201875
Jan. 30, 2015  (JP) ................ 2015-017679

(51) Int. Cl.
C12N 5/00    (2006.01)
C12M 1/28    (2006.01)
C12N 5/074   (2010.01)
C12N 5/10    (2006.01)
C12M 1/34    (2006.01)
C12M 3/00    (2006.01)

(52) U.S. Cl.
CPC ............ *C12N 5/0696* (2013.01); *C12M 3/00* (2013.01); *C12M 41/40* (2013.01); *C12N 5/10* (2013.01); *C12N 2501/727* (2013.01); *C12N 2525/00* (2013.01); *C12N 2531/00* (2013.01); *C12N 2539/00* (2013.01)

(58) Field of Classification Search
None
See application file for complete search history.

(56) References Cited

U.S. PATENT DOCUMENTS

| | | | | |
|---|---|---|---|---|
| 5,496,722 A | * | 3/1996 | Goodwin | C12M 27/10 435/1.1 |
| 2007/0116676 A1 | | 5/2007 | Kida et al. | |
| 2009/0104695 A1 | * | 4/2009 | Shushan | C12N 5/0606 435/366 |
| 2010/0009442 A1 | | 1/2010 | Sasai et al. | |
| 2010/0189699 A1 | * | 7/2010 | Hattori | A61K 35/34 424/93.7 |
| 2010/0221835 A1 | | 9/2010 | Tanaka et al. | |
| 2012/0083029 A1 | | 4/2012 | Tsumura et al. | |
| 2014/0329317 A1 | * | 11/2014 | Nakatsuji | C12N 5/0606 435/366 |
| 2015/0353884 A1 | | 12/2015 | Ozaki et al. | |

FOREIGN PATENT DOCUMENTS

| | | |
|---|---|---|
| JP | 2008-099662 A | 5/2008 |
| JP | 2009-159887 A | 7/2009 |
| WO | WO-2005-056072 A1 | 6/2005 |
| WO | WO-2006-135103 A1 | 12/2006 |
| WO | WO-2010-143651 A1 | 12/2010 |
| WO | WO-2014-115799 A1 | 7/2014 |

OTHER PUBLICATIONS

96-Well PCR Plate, Semi-Skirted (Case Size)—PCR Consumables, Consumables—Star . . . p. 1 of 3 downloaded Sep. 19, 2019.*
Blaber, E.A., et al., "Mechanical Unloading of Bone in Microgravity Reduces Mesenchymal and Hematopoietic Stem Cell-Mediated Tissue Regeneration", Stem Cell Research, Jun. 2014, vol. 13, No. 2, pp. 181-201.
Imura, Takeshi, et al., "Cell Mass Formation and Neuronal Differentiation Ability Under Simulated Microgravity Environment", Regenerative Medicine (Extra Edition), Journal of the Japanese Society for Regenerative Medicine, 2010, vol. 9, Supplemental, p. 264, col. P-005 (with English Translation).
Kawahara, Yumi, et al., "Attempt to Culture Pluripotent Stem Cells Utilizing Microgravity Environment", Regenerative Medicine (Extra Edition), Journal of the Japanese Society for Regenerative Medicine, 2014, vol. 13, Supplemental, p. 304, col. P-1-192 (with English Translation).
Kawahara, Yumi, et al., "Microgravity Environment and Maintaining Undifferentiated State of Stem Cells—Study using Mouse ES cells", Journal of the Japanese Society for Regenerative Medicine, 2010, vol. 9, Supplemental, p. 269, col. P-025 (with English Translation).
Nakagawa, Masato, et al., "Generation of Induced Pluripotent Stem Cells Without Myc from Mouse and Human Fibroblasts", Nature Biotechnology, Jan. 2008, vol. 26, No. 1, pp. 101-106.
Nakata, Kyosuke, et al., "Effect of Change in Gravity Environment on Cartilage Differentiation Capacity of Human Mesenchymal Stem Cells", 2014, vol. 41, No. 2, pp. 90-91, (with English Translation).

(Continued)

*Primary Examiner* — Maria G Leavitt
(74) *Attorney, Agent, or Firm* — McCarter & English, LLP

(57) ABSTRACT

Provided is a method for efficiently culturing pluripotent stem cells with higher safety. The present invention relates to a method for culturing pluripotent stem cells, the method comprising culturing an isolated pluripotent stem cells in a pseudo-microgravity environment to proliferate the pluripotent stem cells while maintaining the pluripotent stem cells in an undifferentiated state, thereby forming and growing spheroids of the pluripotent stem cells; and a method for inducing differentiation of pluripotent stem cells by using the method.

8 Claims, 11 Drawing Sheets

(56) References Cited

OTHER PUBLICATIONS

Takahashi, Kazutoshi, et al., "Induction of Pluripotent Stem Cells from Mouse Embryonic and Adult Fibroblast Cultures by Defined Factors", Cell, Aug. 25, 2006, vol. 126, pp. 663-676.

Takahashi, Kazutoshi, et al., "Induction of Pluripotent Stem Cells from Adult Human Fibroblasts by Defined Factors", Cell, Nov. 30, 2007, vol. 131, pp. 861-872.

Uemura, Toshimasa, et al., "Automated System of RWV Rotational Bioreactor and Application to Tissue Regeneration", Regenerative Medicine (Extra Edition), Journal of the Japanese Society for Regenerative Medicine, 2009, vol. 8, Supplemental, p. 183, col. O-25-4 (with English Translation).

Uemura, Toshimasa, "Mass Culturing of iPS Cells by Three-Dimensional Culture using RWV Bioreactor", Program and Abstracts of the 27th Annual Meeting of the Japanese Society for Alternatives to Animal Experiments, Nov. 1, 2014, p. 136, col. P-86 (with English Abstract Translation).

Uemura, Toshimasa, "Development of a Method for Mass Culturing of iPS Cells Using Simulated Microgravity Culture by RWV Bioreactor", Abstracts of the 36th Annual Meeting of the Japanese Society for Biomaterials, Nov. 17, 2014, p. 76, col. IC-08 (with English Translation).

Ueno, Mofio, "Marked Improvement of Human ES Cell Culture by the ROCK Inhibitor Y-27632", Journal of Clinical and Experimental Medicine, 2008, vol. 227, No. 4, pp. 254-258, (with English Translation).

Wang, Nanding, et al., "The Simulated Microgravity Enhances Multipotential Differentiation Capacity of Bone Marrow Mesenchymal Stem Cells", Cytotechnology, Jan. 2014, vol. 66, No. 1, pp. 119-131.

Yamazaki, Shinya, et al., "The Rotating Culture System Regulates the Osteogenic Fate of Human Bone Mesenchymal Stem Cells", Proceedings of WWLS (Wellfare, Wellbeing, Life Support), The Japan Society of Mechanical Engineers, Sep. 18, 2010, p. 169 (2A2-3) (with English Translation).

Yuge, Louis, "Development of Stem Cells Culture in Simulated Microgravity Environment", The 24th Bioengineering Conference of The Japan Society of Mechanical Engineers, Jan. 6, 2012, pp. 7C14 (with English Translation).

Translation of International Preliminary Report on Patentability, dated Feb. 28, 2017, based on co-pending PCT International Application No. PCT/JP2015/077824, filed Sep. 30, 2015 (English Translation).

International Search Report, dated Apr. 7, 2016 based on co-pending PCT International Application No. PCT/JP2015/077824, filed Sep. 30, 2015 (English Translation).

* cited by examiner

METHOD FOR CULTURING PLURIPOTENT STEM CELLS

RELATED APPLICATIONS

This application is a national stage application filed under 35 USC 371 of PCT/JP2015/077824, filed Sep. 30, 2015, which claims the benefit of Japanese Patent Application No. 2014-201875, filed Sep. 30, 2014 and Japanese Patent Application No. 2015-017679, filed Jan. 30, 2015, each of which is incorporated herein, in its entirety, by reference.

TECHNICAL FIELD

The present invention relates to a method for culturing pluripotent stem cells.

BACKGROUND ART

Finding of induced pluripotent stem cells (herein, often referred to as "iPS cells") (Non Patent Literatures 1 to 3) has increased the momentum for practical use of regenerative medicine using it. The iPS cells are pluripotent stem cells capable of differentiating into various tissues and organs, as with embryonic stem cells (ES cells), but has many advantages over the embryonic stem cells. For example, embryonic stem cells are established from a fertilized egg and thus involve ethical problems, and in contrast, iPS cells can be established from somatic cells and thus do not develop the ethical problem. In addition, embryonic stem cells often cause rejection after transplantation due to difference of a major histocompatibility antigen (MHC), and in contrast, iPS cells are established from cells from a subject for transplantation and thus rarely cause rejection.

On the other hand, the number of iPS cells in the order of $10^6$, a quantity commonly used in a laboratory, is far from sufficient for using iPS cells in regenerative medicine or the like, and required to be in the order of $10^9$ to $10^{10}$ for clinical use. However, techniques for mass culture of iPS cells have not been fully established. To culture iPS cells while they are maintained in an undifferentiated state, it is generally considered to be necessary to culture them on feeder cells such as primary cultures of mouse embryonic fibroblast (MEF) and STO cells. However, contamination with a feeder cell constitutes a significant obstacle to use of iPS cells for regenerative medicine. In view of this, studies on a feeder-free cell culture method have been also conducted, and methods enabling cell culture without any feeder cell have been developed, such as a method of culturing iPS cells on the surface of a base material coated with Matrigel and a culture method utilizing a coating with laminin or a partial peptide of laminin. In addition, bag culture has been performed in place of common dish culture. However, it is necessary to repeat culture on a base material with a coating even in a feeder-free culture system, and thus the culture process is complicated and the cost of culture significantly increases, which causes a serious problem of huge cost to treat one patient. A method for efficiently mass-culturing stable iPS cells retained in an undifferentiated state has not been developed yet.

To construct a three-dimensional tissue from cells, it is typically needed to perform three-dimensional culture with an appropriate scaffold material, or to perform spinner culture. However, conventional spinner culture applies a strong mechanical stimulus and significant damage to cells, and thus it is difficult to obtain a large tissue, and even if a large tissue is obtained, the inside often undergoes necrosis.

As a countermeasure against this, there exists a series of bioreactors designed to optimize the weight. An RWV (Rotating Wall Vessel) bioreactor, one of such bioreactors, is a rotary bioreactor with gas exchange function developed by NASA. The present inventors have conducted research and development of, for example, a technique of cartilage regeneration from bone marrow cells, etc., by three-dimensional culture with the RWV bioreactor (Patent Literatures 1 to 3).

In contrast, a method for three-dimensionally culturing iPS cells, growth of which in an undifferentiated state is considered to be difficult in an environment without scaffolds such as feeder cells or a coating material, in an efficient manner has not been developed yet.

CITATION LIST

Patent Literature

Patent Literature 1: International Publication No. WO2005/056072
Patent Literature 2: JP Patent Publication (Kokai) No. 2009-159887
Patent Literature 3: International Publication No. WO2006/135103

Non Patent Literature

Non Patent Literature 1: Takahashi, K. and Yamanaka, S., (2006) Cell 126, p. 663-676
Non Patent Literature 2: Takahashi K., et al., (2007) Cell 131, p. 862-872
Non Patent Literature 3: Nakagawa M., et al., (2008) Nat. Biotechnol., 26(1): p. 101-106

SUMMARY OF INVENTION

Technical Problem

An object of the present invention is to provide a method for efficiently culturing pluripotent stem cells with higher safety.

Solution to Problem

As a result of diligent research to solve the aforementioned problems, the present inventors found that culturing pluripotent stem cells in a pseudo-microgravity environment allows for proliferation of the pluripotent stem cells maintained in an undifferentiated state to form spheroids even in the absence of feeder cells or a coating material, and thus completed the present invention. Since iPS cells have been considered to grow on feeder cells or on a coating material such as Matrigel and to be difficult to grow iPS cells in an environment in the absence of feeder cells or a coating material, the finding by the present inventors that iPS cells can be mass-cultured in a simple manner without such a cell scaffold material to produce spheroids is quite surprising. In the present invention, this culture method allows for proliferation of pluripotent stem cells in a closed system, which has a low contamination risk, and thus the present invention can also provide enhanced safety.

More specifically, the present invention encompasses the followings.

[1] A method for culturing pluripotent stem cells, the method comprising: culturing isolated pluripotent stem cells in a pseudo-microgravity environment to proliferate the pluripotent stem cells while maintaining the pluripotent stem cells in an undifferentiated state, thereby forming and growing spheroids of the pluripotent stem cells.

[2] The method according to the above [1], wherein the pluripotent stem cells are iPS cells.

[3] The method according to the above [1] or [2], wherein the culturing is performed in the absence of a cell scaffold material.

[4] The method according to any one of the above [1] to [3], wherein the pluripotent stem cells are seeded at a cell density of $4 \times 10^4$ to $6 \times 10^4$ cells/cm$^3$.

[5] The method according to any one of the above [1] to [4], wherein the culturing is performed in the presence of an apoptosis inhibitor.

[6] The method according to the above [5], wherein the apoptosis inhibitor is a ROCK inhibitor.

[7] The method according to any one of the above [1] to [6], wherein the pseudo-microgravity environment is an environment in which an object is subjected to a gravity corresponding to $1/10$ to $1/100$ of the earth's gravity in time average.

[8] The method according to any one of the above [1] to [7], wherein the pseudo-microgravity environment is obtainable by using a uniaxial rotary bioreactor capable of achieving a pseudo-microgravity environment on earth by canceling out the earth's gravity with stresses caused by rotation.

[9] The method according to the above [8], wherein the uniaxial rotary bioreactor is an RWV bioreactor.

[10] The method according to any one of the above [1] to [9], further comprising dispersing cells from the spheroid and culturing the cell.

[11] The method according to the above [10], comprising performing one cycle of steps of disrupting the spheroids by passing the spheroid through a filter having a filter mesh size of 40 to 100 μm once or more times and culturing the disrupted spheroids in a pseudo-microgravity environment, thereby forming and growing spheroids; or repeating the cycle two or more times.

[12] The method according to the above [11], wherein the disrupted spheroids are cultured in the pseudo-microgravity environment for 2 to 7 days to form and grow spheroids.

[13] A method for inducing differentiation of pluripotent stem cells, the method including performing the method according to any one of the above [1] to [12], and further culturing resulting pluripotent stem cells and/or spheroids in a differentiation-inducing medium.

[14] The method according to the above [13], wherein the culturing in the differentiation-inducing medium is performed in a pseudo-microgravity environment.

The present specification encompasses the contents disclosed in JP Patent Application Nos. 2014-201875 and 2015-017679, to which the present application claims priority.

Advantageous Effects of Invention

The present invention enables efficient proliferation of pluripotent stem cells maintained in an undifferentiated state with higher safety.

DESCRIPTION OF EMBODIMENTS

Figure 1:
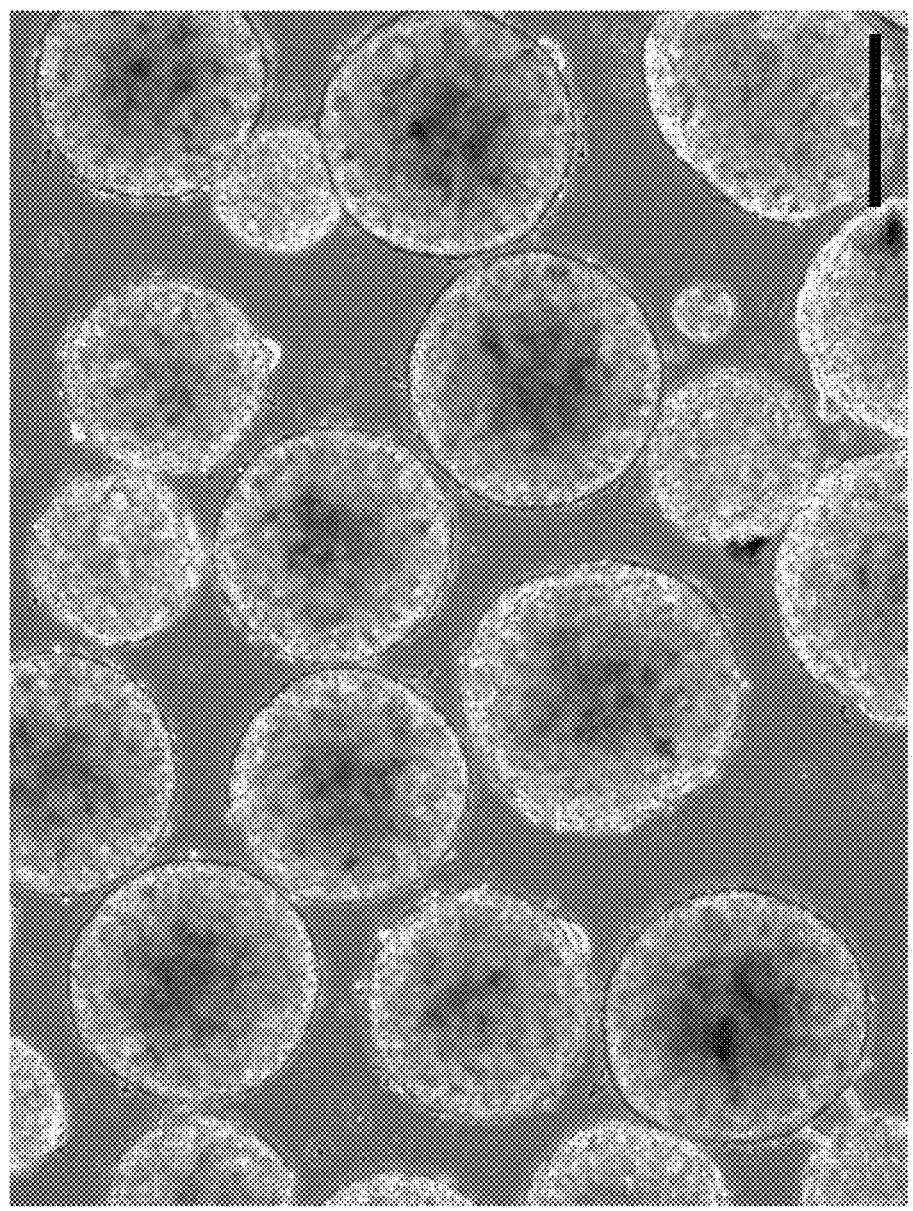
FIG. 1 shows a photograph of a phase contrast image of spherical spheroids produced by rotary-culturing 253G1 cells with an RWV bioreactor in the presence of a ROCK inhibitor for 3 days. The bar therein indicates 500 μm.

Hereinafter, the present invention will be described in detail.

The present invention provides a method for culturing (proliferating) pluripotent stem cells, comprising culturing isolated pluripotent stem cells in a pseudo-microgravity environment to proliferate the pluripotent stem cells while the pluripotent stem cells are retained in an undifferentiated state.

1. Pseudo-Microgravity Environment and Bioreactor

In the present invention, "pseudo-microgravity environment" refers to a simulated microgravity environment which imitates a microgravity environment in the space or the like. Such a pseudo-microgravity environment is achieved, for example, by canceling out the earth's gravity with stresses caused by rotation. A rotating object is subjected to a force shown by the vector sum of the earth's gravity and stresses, and the magnitude and direction of the force varies over time. Eventually, it follows that a rotating object is only subjected to a gravity much smaller than the earth's gravity (1 g) in time average, and thus a "pseudo-microgravity environment" which is very similar to the space is achieved. The "pseudo-microgravity environment" in the present invention is preferably controlled so that pluripotent stem cells can proliferate in a culture medium (or medium) without sinking and a three-dimensional cell aggregate (spheroid) produced suspends in the solution without sinking. For example, a culture system may be rotated at a rotation speed such that the effect of the earth's gravity on cells is minimized. Specifically, it is preferred to employ a rotation speed such that the microgravity applied to cultured cells is reduced to a gravity corresponding to approximately 1/10 to 1/100 of the earth's gravity (1 g) in time average.

In the present invention, a pseudo-microgravity environment can be achieved by using a rotary bioreactor. Examples of such bioreactors include an RWV (Rotating-Wall Vessel: U.S. Pat. No. 5,002,890), an RCCS (Rotary Cell Culture System™: Synthecon, Incorporated), and a 3D-clinostat, and bioreactors disclosed in JP Patent Publications Nos. 8-173143A (1996), 9-37767A (1997), and 2002-45173A. In the present invention, it is preferred to use a uniaxial rotary bioreactor. This is because multiaxial rotary bioreactors (e.g., twin-axial clinostats) cannot minimize shear stress and a sample itself simultaneously rotates, and thus a sample cannot be brought into suspension in the vessel in contrast to the case of a uniaxial rotary bioreactor. Especially, an RWV and an RCCS are superior in that they have gas exchange function.

An RWV bioreactor, which is a uniaxial rotary bioreactor with gas exchange function developed by NASA, is a uniaxial rotary culture apparatus in which cells are seeded in a lateral cylindrical bioreactor filled with a culture medium and then cultured while rotating the bioreactor around the horizontal axis of the cylinder. In an RWV bioreactor, the earth's gravity is canceled out due to stresses by rotation and a microgravity environment whose gravity is much smaller than the gravity on earth (approximately 1/100) is achieved, and as a result cells proliferate in a suspended state in a culture medium, which enables three-dimensional culture. In such a pseudo-microgravity environment, pluripotent stem cells suspended in a culture medium can efficiently proliferate and aggregate to form spheroids (three-dimensional cell aggregates; typically spherical, cell masses). In addition, culture in a pseudo-microgravity environment allows a spheroid of pluripotent stem cells to develop into a larger spheroid.

The culture container (e.g., a vessel) to culture pluripotent stem cells in a pseudo-microgravity environment is not limited, and a culture container which has any shape or volume and is applicable to uniaxial rotary bioreactors such as an RWV bioreactor may be used. The culture container (e.g., a vessel) may be, but is not limited to, a culture container having a volume of 5 mL to 5000 mL, 10 mL to 2000 mL, or 10 mL to 100 mL.

A preferred rotation speed when an RWV bioreactor is used may be appropriately set in accordance with the diameter of the vessel and the size or mass of a spheroid to be produced. In the case that a vessel with a volume of up to approximately 100 mL, for example, an RWV vessel with a diameter of 5 cm (volume: 10 mL) is used, however, it is preferred to set the rotation speed to approximately 5 to 15 rpm, 7 to 15 rpm, for example, 7.5 to 8.5 rpm or 6 to 8.5 rpm. If the rotation speed is constant, the flow rate increases in proportion to the radius from the rotational center. Accordingly, in the case that a vessel with a larger volume, for example, a vessel with a large volume and diameter such as 250 mL, 500 mL, 1000 mL, or 2000 mL vessel is used, those skilled in the art could regulate the rotation speed to an appropriate speed in a decreasing way. When cells are cultured at such a rotation speed, the gravity acting on the cells in the vessel is substantially approximately 1/10 to 1/100 of the gravity on earth (1 g), and thus spheroids can be maintained in a suspended state without sinking.

2. Pluripotent Stem Cells and Culturing Conditions Therefor

The pluripotent stem cells to be cultured by using the method according to the present invention is not limited, but may be preferably an induced pluripotent stem cells, which is also called "iPS cells", or embryonic stem cells, which are also called "ES cells". The iPS cells are pluripotent stem cells induced by introducing reprogramming factors (typically, introducing one or more reprogramming-inducing genes) into somatic cells to reprogram them, and well known to those skilled in the art. Examples of reprogramming factors include, but not limited to, members of the Oct family, the Klf family, the Sox family, the Myc family, the Nanog family, and the Lin family and the like. Specific examples of reprogramming factors include, but not limited to, Oct3/4, Klf4, Klf2, Sox1, Sox2, Sox3, Sox15, Sox17, c-Myc, N-Myc, L-Myc, T58A, Nanog, Lin28, Fbx15, ERas, ECAT15-2, Tcl1, β-catenin, Lin28b, Sall1, Sall4, Esrrb, Nr5a2, Tbx3, p53shRNA, and Glis1. It is preferred to introduce at least an Oct family member, especially Oct3/4, into somatic cells. Introduction of a reprogramming factor can be performed by introducing a gene encoding a reprogramming factor (reprogramming-inducing gene) into somatic cells.

iPS cells can be produced, for example, by introducing an Oct family gene, a Klf family gene, and an Sox family gene and/or an Myc family gene (e.g., Oct3/4, Sox2, and Klf4). iPS cells may be produced by using another method. Typically, iPS cells are derived from an animal, and preferably derived from a mammal, including primates such as humans and monkeys, rodents such as mice and rats, dogs, cats, rabbits and the like. The iPS cells may be derived from any tissue (somatic cell), which includes, but not limited to, skin, bone marrow, nose, gastrointestinal tract, liver and the like. The ES cells are pluripotent cells obtained by culturing the inner cell mass of a blastocyst. Although iPS cells and ES cells are available, for example, from RIKEN BioResource Center Cell Engineering Division (RIKEN BRC CELL BANK) (Japan), ATCC (American Type Culture Collection), and iPS Academia Japan, Inc. (Japan), those skilled in the art could produce them by a conventional method. Here, the term "isolated" in the context of pluripotent stem cells in the present invention means that the cell is a cell removed from a living body or a cell line produced from a cell removed from a living body. The "isolated" pluripotent stem cell may be a single cell or be in a cell mass, a spheroid, or the like.

In the method according to the present invention, pluripotent stem cells can be rotary-cultured using any ES/iPS medium (undifferentiation-maintaining medium) for proliferation of the cells and formation of spheroids. Examples of such media include, but not limited to, an mTeSR1 medium and a TeSR1 medium (STEMCELL Technologies Inc.); an Essensial 8™ medium and an Essential 6™ medium (Gibco); and a StemPro®-34 SFM (Life Technologies).

In one embodiment, pluripotent stem cells are seeded in a culture medium at a cell density of, for example, $1 \times 10^4$ to $1 \times 10^5$ cells/cm$^3$, more preferably $3 \times 10^4$ to $8 \times 10^4$ cells/cm$^3$, even more preferably $4 \times 10^4$ to $6 \times 10^4$ cells/cm$^3$, and cultured (typically, rotary-cultured) in a pseudo-microgravity environment, and thereby efficient cell proliferation and spheroid production (formation and growth of spheroids) can be provided. It is particularly preferred to seed at the cell density, for example, in a vessel with a diameter of 4 to 6 cm such as a vessel with a diameter of 5 cm (volume: 10 mL). In seeding at such a cell density, however, the vessel is not limited to vessels with any of the above sizes, and for example, even a vessel with a volume of 10 to 2000 mL allows for effective proliferation of pluripotent stem cells.

Pluripotent stem cells prepared by a conventional method may be used to seed. For example, pluripotent stem cells cultured under normal culturing conditions may be detached, for example, by using any mechanical, chemical, or biological cell dispersion method after culture and then used for the above rotary culture or the like. Specifically, the cells may be dispersed by using EDTA (e.g., 1 to 10 mM EDTA), TryPLE™ Select, Accutase™, collagenase. Dispase, trypsin, trypsin/EDTA, trypsin/collagenase, ReLeSR™ (STEMCELL Technologies Inc.), or the like as a cell detachment solution, but the cell detachment solution is not limited thereto. Alternatively, spheroids of pluripotent stem cells formed through suspension culture may be mechanically disrupted by filtering or the like to disperse the cells and then used for the above rotary culture or the like.

Pluripotent stem cells may be separated and dispersed into small spheroids (cell masses) each consisting of approximately 3 to 1,000 cells, preferably approximately 5 to 600 cells, more preferably 5 to 300 cells, for example, approximately 30 to 200 cells, 10 to 100 cells, or 20 to 40 cells, and seeded and subjected to culture in a pseudo-microgravity environment such as rotary culture. In the first culture in a pseudo-microgravity environment (culture after the first passage), pluripotent stem cells may be separated and dispersed into small spheroids (cell masses) each consisting of preferably 5 to 300 cells, more preferably 10 to 100 cells, even more preferably 20 to 40 cells, and seeded and subjected to culture in a pseudo-microgravity environment such as rotary culture. A small spheroid of pluripotent stem cells produced through chemical disrupting with a cell detachment solution or the like typically has a diameter of smaller than 300 μm, for example, a diameter of approximately 50 to 200 μm. Culturing pluripotent stem cells seeded in a form of small spheroids in a pseudo-microgravity environment allows for acceleration of formation and growth of spheroids. The term "small spheroid" used herein refers to a relatively small-sized cell mass composed of a relatively small number of cells, and encompasses a cell mass of typically approximately 3 to 1,000 cells, for example, 5 to 600 cells, 30 to 200 cells, 10 to 100 cells, or 20 to 40 cells. The small spheroid may have a spherical or elongate shape, or may have another shape. Alternatively, pluripotent stem cells in a form of spheroids or pluripotent stem cells dispersed into individual cells may be cultured (e.g., rotary-cultured) in a pseudo-microgravity environment as described above.

Culture of pluripotent stem cells in a pseudo-microgravity environment such as rotary culture may be performed in the presence of an apoptosis inhibitor. As an apoptosis inhibitor, a ROCK (Rho-associated kinase) inhibitor can be preferably used, but the apoptosis inhibitor is not limited thereto. The ROCK inhibitor is known to be effective for survival of ES cells and contribute to inhibition of apoptosis (Watanabe K., Nat. Biotechnol., (2007) 25(6), p. 681-686; Ohgushi M., et al., Cell Stem Cell, (2010) 7(2), p. 225-239). Examples of ROCK inhibitors include Y27632 ((R)-(+)-trans-N-(4-pyridyl)-4-(1-aminoethyl)-cyclohexanecarboxamide.2HClH$_2$O) (e.g., Calbiochem, Wako Pure Chemical Industries, Ltd.), and Fasudil (1-(5-isoquinolinesulfonyl)homopiperazine hydrochloride) (e.g., Calbiochem). In one embodiment, the concentration of an apoptosis inhibitor in a culture medium may be 1 μM to 100 μM, preferably 3 μM to 30 μM, and more preferably 5 μM to 15 μM. Culture in the presence of an apoptosis inhibitor allows for acceleration of formation and growth of spheroids of pluripotent stem cells. The term "spheroid" in the present invention refers to a cell mass as an aggregate of many cells, and refers to a cell mass typically having a diameter of 300 μm or larger, for example, a diameter of 300 to 2000 μm.

The culturing temperature for pluripotent stem cells is not limited, but is preferably 36.0 to 38.0° C., and more preferably 36.5 to 37.5° C. Rotary culture with a bioreactor may be performed preferably for 2 to 7 days, more preferably 2 to 5 days such as 3 to 5 days, even more preferably 3 to 4 days, but the period is not limited thereto. In the case that culture is performed for a longer period, culture may be performed by subculturing cells preferably every 2 to 7 days, more preferably 2 to 5 days such as 3 to 5 days, even more preferably 3 to 4 days, but the interval is not limited thereto.

In the present invention, the above-described culture can provide mass production of spheroids (primarily, spherical spheroids) of pluripotent stem cells in a culture medium. In one embodiment, the diameter of spheroids obtained after culturing for 3 days is primarily in the range of 300 to 1000 μm, and the most frequent diameter of them is in the range of 700 to 900 μm.

Pluripotent stem cells or cells constituting spheroids obtained through the above-described culture are maintained in an undifferentiated state. Maintenance of an undifferentiated state can be confirmed by detecting the expression of an undifferentiation marker with flow cytometry or the like. Examples of undifferentiation markers include, but not limited to, SSEA-4, TRA-1-60, Nanog, Oct3/4, Sox2, REX-1, LIN28, LEFTB, GDF3, ZFP42, FGF4, ESG1, DPPA2, TERT, KLF4, and c-Myc.

To confirm the undifferentiated state of a cell, it is more preferred to analyze the expression states of undifferentiation marker genes. Analysis of the expression states of undifferentiation marker genes can be preferably performed, for example, by using quantification with real-time PCR.

Moreover, the culture method according to the present invention allows for proliferating pluripotent stem cells while maintaining the cells in an undifferentiated state through rotary culture of the cell, without use of any cell scaffold material. In the present invention, the term "cell scaffold material" refers to any cell scaffold material (scaffold) that can be used for cell culture such as collagen, polymers, gels, glass, plastics, fibers, films, and beads.

In the present invention, rotary culture with a rotary bioreactor capable of achieving a pseudo-microgravity environment such as an RWV bioreactor allows for proliferation of pluripotent stem cells in a closed system, which has a low contamination risk, and thus the present invention can also provide enhanced safety.

In the culture method according to the present invention, spheroids of pluripotent stem cells produced through culture in a pseudo-microgravity environment may be separated and dispersed into fewer cells, for example, into small spheroids, and further cultured. As described above, separation and dispersion of cells from spheroids can be performed, for example, by using any mechanical, chemical, or biological method.

Further culturing (typically, rotary-culturing) cells dispersed from spheroids in the above-described pseudo-microgravity environment allows for mass proliferation of cells to produce numerous spheroids. Alternatively, cells dispersed from spheroids may be cultured on feeder cells by using a common method for culturing stem cells, and thereby numerous cell colonies can be produced.

In a preferred embodiment of the present invention, it is also preferred to perform one cycle of the steps of disrupting spheroids (typically, spherical spheroids) produced through culture in a pseudo-microgravity environment in accordance with the above-described method by any mechanical (dynamical), chemical, or biological method, further culturing small spheroids thus produced in a pseudo-microgravity environment, thereby forming and growing spheroids; or repeat the cycle two or more times (a plurality of times, for example, 2 to 30 times). Small spheroids to be further cultured in a pseudo-microgravity environment may be a mixture of small spheroids obtained by using different disrupting methods. In one preferred embodiment, for example, the steps of disrupting spheroids produced through culture in a pseudo-microgravity environment in accordance with the above-described method typically by passing the spheroids through a filter, and further culturing small spheroids obtained by the mechanical (dynamical) disrupting in a pseudo-microgravity environment, thereby forming and growing spheroids may be performed once or repeated two or more times. Filtering of spheroids may be performed under pressure by using a pipette or the like. Filters having a filter mesh size which enables a disruption of spheroids produced into small spheroids with a smaller size can be used, and filters having a filter mesh size of 40 to 100 µm, preferably 60 to 80 µm, for example, 70 µm are preferred. In general, a small spheroid obtained by disrupting through filtering has an elongate shape. For example, a small spheroid obtained by disrupting through filtering with a 70 µm filter generally has a size comparable to or larger than those of small spheroids obtained by chemical disrupting. Spheroids may be disrupted by passing the spheroids through a filter once or two or more times (a plurality of times, for example, 2 to 30 times). In the case that disrupting through filtering is performed two or more times, filters to be used in the filterings may have an identical filter mesh size or a different filter mesh size. After spheroids are disrupted by passing the spheroids through a filter, for example, the disrupted spheroids (small spheroids) may be further disrupted by passing the spheroids through a filter having a larger filter mesh size, and thereby the sizes (especially, the major axis) of the small spheroids prepared can be uniformed in a narrower range. The culturing period for the disrupted spheroids (small spheroids) in a pseudo-microgravity environment is 2 to 7 days, preferably 2 to 5 days, and more preferably 3 to 5 days or 3 to 4 days, for example, but is not limited thereto. The culture volume in each culturing step in a pseudo-microgravity environment, i.e., the size of a culture container and the volume of medium may be identical or different among culturing steps. In the case of mass culture, the culture volume may be scaled-up as culture is repeated. In the present invention, the method by repeating a cycle including forming and growing spheroids through culture in a pseudo-microgravity environment, disrupting the spheroids thus produced, and reseeding the small spheroids generated through disrupting enables proliferation of pluripotent stem cells such as iPS cells while the pluripotent stem cells are maintained in an undifferentiated state for a very long period. This further facilitates mass production of pluripotent stem cells such as iPS cells.

3. Induction of Differentiation

After pluripotent stem cells (proliferated pluripotent stem cells, or pluripotent stem cells dispersed from produced spheroids) or spheroids cultured are obtained by the method according to the present invention, differentiation of the cells may be induced. For example, culturing pluripotent stem cells in a differentiation-inducing medium, for example, in an ectodermal differentiation medium, a mesodermal differentiation medium, or an endodermal differentiation medium enables induction of differentiation of the cells into an ectoderm, a mesoderm, or an endoderm, respectively. Ectoderm differentiation media, mesoderm differentiation media, and endoderm differentiation media are commercially available, and examples thereof include those included in the triploblastic differentiation kit, Stem Cell Kit: Human Pluripotent Stem Cell Functional Identification Kit (R&D Systems, Inc.). The pluripotent stem cell to be seeded in a differentiation-inducing medium may be in a small spheroid or dispersed single cells. Culture in a differentiation-inducing medium may be performed on feeder cells such as an MEF or a cell scaffold material such as a coating material, or may be performed as the above-described rotary culture in a pseudo-microgravity environment. Culture in a differentiation-inducing medium can induce differentiation of pluripotent stem cells into an intended germ layer or cells, and thus enables production of cells differentiated from pluripotent stem cells. Accordingly, the present invention also provides a method for inducing differentiation of pluripotent stem cells (a method for producing cells differentiated from pluripotent stem cells), the method comprising performing the above-described method for culturing pluripotent stem cells, and further culturing the resulting pluripotent stem cells (proliferated pluripotent stem cells or pluripotent stem cells dispersed from a spheroid produced) and/or spheroids in a differentiation-inducing medium. Culture in a differentiation-inducing medium may be performed as the above-described culture in a pseudo-microgravity environment (e.g., rotary culture), or may be performed by another cell culture method used for induction of differentiation.

Differentiation into an ectoderm, a mesoderm, and an endoderm can be confirmed by detecting the expression of marker genes for each of them. Examples of ectoderm marker genes include Otx2, Nestin, and TP63; examples of mesoderm marker genes include Brachyury; and examples of endoderm marker genes include Sox17, AFP, GATA-4, and PDX-1. If a strong expression is shown for any of these marker genes, the expression indicates differentiation into the corresponding germ layer.

In one preferred embodiment, a spheroid of pluripotent stem cells obtained by using the method according to the present invention, that is, a method for culturing pluripotent stem cells in a medium for maintaining an undifferentiated state with the above-described culture in a pseudo-microgravity environment, may be further cultured in a differentiation-inducing medium, thereby inducing differentiation of the cells in the spheroid while the spheroid form is retained. Culture in a differentiation-inducing medium may be performed as culture in a pseudo-microgravity environment, or may be performed by another cell culture method used for induction of differentiation. After a spheroid is obtained through culture in a medium for maintaining an undifferentiated state in a pseudo-microgravity environment (e.g., rotary culture), for example, the medium is replaced with a differentiation-inducing medium and culture in a pseudo-microgravity environment is continued, and thereby the pluripotent stem cells (undifferentiated cells) constituting the spheroid can be differentiated into intended cells (cells which the differentiation-inducing medium used is intended to produce). Thus, a spheroid comprising cells differentiated from pluripotent stem cells can be produced. Alternatively, after a spheroid is obtained through culture in a medium for maintaining an undifferentiated state in a pseudo-microgravity environment (e.g., rotary culture), the spheroid may be transferred into a differentiation-inducing medium, and cultured, for example, subjected to culture in a pseudo-microgravity environment (e.g., rotary culture) to differentiate the pluripotent stem cells (undifferentiated cells) constituting the spheroid into intended cells. Accordingly, the present invention also provides a method for inducing differentiation of pluripotent stem cells, the method comprising performing the above-described method for culturing pluripotent stem cells, and further culturing the resulting spheroid in a differentiation-inducing medium; and a method for producing a spheroid comprising differentiated cells from pluripotent stem cells by using the method.

In the method according to the present invention, any differentiation-inducing medium intended to induce differentiation into predetermined cells may be used to induce differentiation of pluripotent stem cells. Examples of such differentiation-inducing media may include neuronal differentiation media, osteoblast differentiation media, cardiomyocyte differentiation media, adipocyte differentiation media, and intestinal epithelial cell differentiation media. For example, culturing pluripotent stem cells or spheroids by using a neuronal differentiation medium as a differentiation-inducing medium enables a differentiation of the pluripotent stem cells into neural cells. Alternatively, the differentiation-inducing medium may be an ectodermal differentiation medium, a mesodermal differentiation medium, or an endodermal differentiation medium. Various commercially available products may be used as these differentiation-inducing media.

EXAMPLES

Hereinafter, the present invention will be described in more detail with referring to Examples. However, the technical scope of the present invention is never limited to the Examples.

In the following Examples, 253G1 cells were used as human induced pluripotent stem cells (hiPSCs). The 253G1 cells (with Oct3/4, Sox2, and Klf4 introduced thereinto; Non Patent Literature 3) were purchased from RIKEN BioResource Center Cell Engineering Division (RIKEN BRC CELL BANK) (Japan) under the cell number HPS0002.

[Example 1] Production of Spheroid from Induced Pluripotent Stem Cells (iPS Cells) Through Three-Dimensional Culture with RWV Bioreactor (1) Construction of Spherical Spheroid By using a 6 cm or 10 cm culture dish coated with Matrigel (BD Matrigel™, BD Biosciences), 253G1 cells were cultured in an mTeSR1 (STEMCELL Technologies Inc.), a medium for maintaining human ES/iPS cells while the culture medium was replaced with fresh medium every day, and subcultured by using 5 mM EDTA and 0.5× TrypLE™ Select (Life Technologies).

Figure 2:
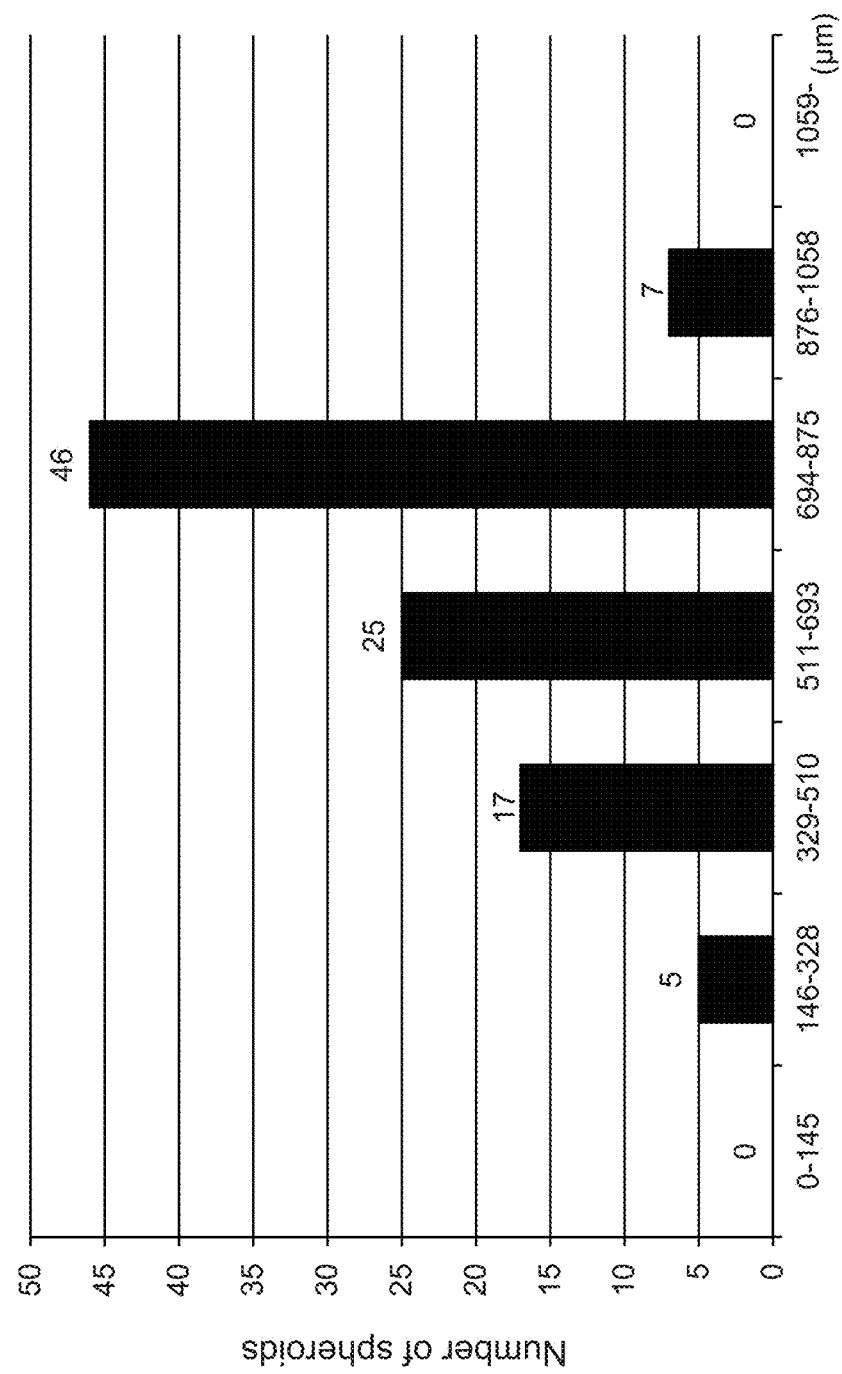
FIG. 2 shows the diameter distribution of spherical spheroids produced by rotary-culturing 253G1 cells with an RWV bioreactor in the presence of a ROCK inhibitor for 3 days.

To perform three-dimensional culture, 253G1 cells to be seeded were detached into small spheroids (loose cell masses each having a diameter of approximately 50 μm to 200 μm) each consisting of 20 to 40 cells with 5 mM EDTA. The detached $4.9 \times 10^5$ 253G cells (small spheroids obtained through chemical disrupting) were seeded in an mTeSR1 medium (10 mL) containing the ROCK (Rho-associated kinase) inhibitor Y27632 (Wako Pure Chemical Industries, Ltd., 10 μM) or an mTeSR1 medium (10 mL) free of the ROCK inhibitor Y27632 in a 10 mL RWV vessel (diameter: 5 cm; Synthecon, Incorporated), and rotary-cultured with an RWV bioreactor (Synthecon, Incorporated) at 37° C. and 8 rpm for 3 days. After culturing, a photograph of a phase contrast image of spherical spheroids produced in the culture medium was taken with the inverted microscope Axio Observer (Carl Zeiss) (FIG. 1). In addition, the diameter of each spherical spheroid was measured, and the size distribution was investigated (FIG. 2).

Subsequently, the spherical spheroids were collected, and disrupted by pipetting with a pipette to disperse the cells. The number of the cells was counted by using the automated cell counter, Countess™ (Invitrogen). From the total number of the cells in the culture medium, the proliferation rate relative to the number of the cells seeded ($4.9 \times 10^5$ cells) was calculated (total number of cells/$4.9 \times 10^5$ cells).

In the vessel with the ROCK inhibitor-containing medium, numerous spherical spheroids were formed (FIG. 1). The total number of cells was $3.1 \times 10^6$, and the proliferation rate was 6.5-fold. The distribution of the diameters of the spherical spheroids had a peak in 700 to 900 μm (FIG. 2). In contrast, in the vessel with the ROCK inhibitor-free medium, no spherical spheroids were formed and a suspension containing only single cells was prepared.

These results demonstrate that rotary culture in a ROCK inhibitor-containing medium with an RWV bioreactor enables production of a spherical spheroid from iPS cells.

(2) Investigation on ROCK Inhibitor Concentration

To determine a more suitable ROCK inhibitor concentration, 253G1 cells were rotary-cultured for 3 days under the same conditions as in the above except that three ROCK inhibitor concentrations (3 μM, 10 μM, or 30 μM) were used. After culturing, the number of spherical spheroids formed was 10 in the case of 3 μM, 50 in the case of 10 μM, and 20 in the case of 30 μM.

These results suggest that ROCK inhibitor concentration conditions of 10 μM are the most suitable among the three conditions for obtaining many spherical spheroids.

(3) Investigation on the Number of Cells to be Seeded

To determine a more suitable number of cells to be seeded, 253G1 cells detached into small spheroids each consisting of approximately 20 to 40 cells with 5 mM EDTA and TrypLE™ Select were seeded at $4.27 \times 10^5$, $8.55 \times 10^5$, or $1.28 \times 10^6$ cells in a 10 mL RWV vessel, and rotary-cultured for 5 days in an mTeSR1 medium containing or free of the ROCK inhibitor Y27632 (10 μM) by the same method as in the above (1). After culturing, the number of the cells was counted and the proliferation rate was calculated in the same manner as in the above. Table 1 below shows the results.

TABLE 1

| Number of cells seeded (cells)/10 mL vessel | ROCK inhibitor | Proliferation rate |
|---|---|---|
| $4.27 \times 10^5$ | Free | 1.5-fold |
| $8.55 \times 10^5$ | Free | 1.12-fold |
| $4.27 \times 10^5$ | 10 μM | 4.78-fold |

TABLE 1-continued

| Number of cells seeded (cells)/10 mL vessel | ROCK inhibitor | Proliferation rate |
|---|---|---|
| $8.55 \times 10^5$ | 10 µM | 1.93-fold |
| $1.28 \times 10^6$ | 10 µM | 1.43-fold |

The same experiment was further repeated a plurality of times, and the result showed that $4 \times 10^5$ to $6 \times 10^5$ cells seeded per 10 mL medium, in other words, an initial cell density of $4 \times 10^4$ to $6 \times 10^4$ cells/cm³ provided a significantly high proliferation rate. Although cell proliferation was found also for the ROCK inhibitor-free medium, the proliferation rate was significantly increased in the ROCK inhibitor-containing medium.

Further, the 253G1 cells detached into small spheroids each consisting of approximately 20 to 40 cells with only 5 mM EDTA were seeded in a 10 mL RWV vessel at a number of cells seeded in the above preferred range, and rotary-cultured in a 10 µM ROCK inhibitor Y27632-containing mTeSR1 medium (10 mL) for 3 days. Table 2 shows examples of results obtained using only 5 mM EDTA for cell detachment.

TABLE 2

| | Cells seeded (cells) | Number of only cells of spheroids (proliferation rate) Number of spheroids | Total number of cells (proliferation rate) |
|---|---|---|---|
| 1st | $4.9 \times 10^5$ | $2.4 \times 10^6$ (4.9-fold) approximately 130 spheroids | $3.1 \times 10^6$ (6.5-fold) |
| 2nd | $4.1 \times 10^5$ | $1.4 \times 10^6$ (3.41-fold) approximately 100 spheroids | $2.4 \times 10^6$ (5.85-fold) |

These results demonstrate that a particularly good proliferation rate can be obtained in the above preferred range of the number of cells to be seeded, irrespective of the cell detachment conditions.

[Example 2] Characterization of iPS Cells Cultured with RWV Bioreactor

In accordance with the method described in Example 1, the 253G1 cells detached with 5 mM EDTA were seeded in a 10 mL vessel, and rotary-cultured in a 10 µM ROCK inhibitor Y27632-containing mTeSR1 medium with an RWV bioreactor for 3 days. After culturing, spheroids produced were treated with Accutase™ to be dispersed into single cells, and the cells were seeded on a 24-well plate coated with Matrigel, and cultured for 3 days. After culturing, flow cytometry analysis was performed to analyze the expression of pluripotent stem cell markers in the 253G1 cells. Flow cytometry was performed by using the flow cytometer, Attune® Acoustic Focusing Cytometer (Applied Biosystems) with fluorescence-labeled antibodies to stain pluripotent stem cells (anti-SSEA-4 antibody: Alexa Fluor488 anti-human SSEA4 (Cat330441, BioLegend, Inc.); and anti-TRA-1-60 antibody: PE anti-human TRA-1-60 (Cat330609, BioLegend, Inc.)) (test sample). For a negative control, Alexa Fluor 488 Mouse IgG3, KIso Type Ctrl (Cat401323, BioLegend, Inc.), and PE Mouse IgM, κIsoType Ctrl (Cat401609, BioLegend, Inc.) were used.

Figure 3:
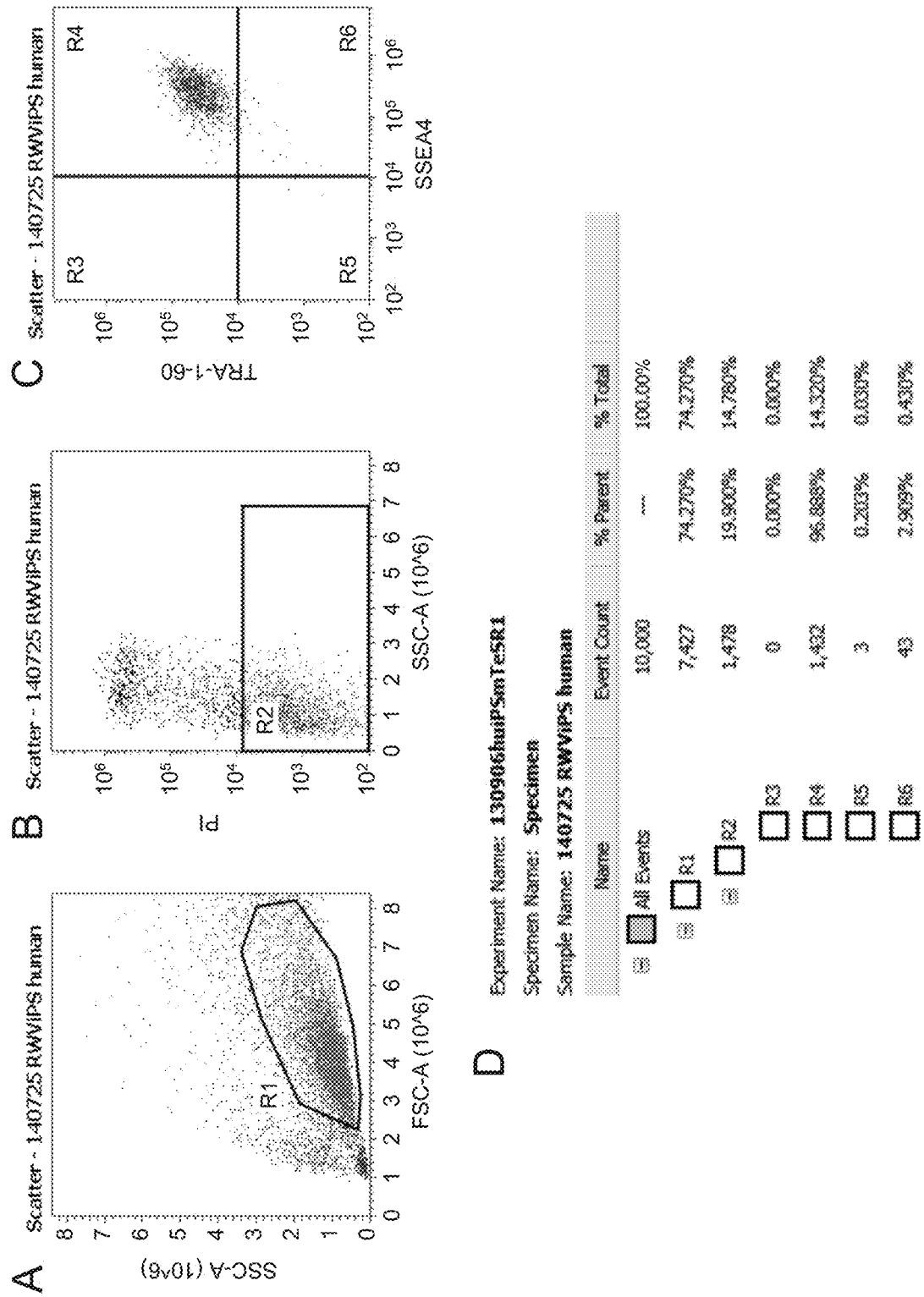
FIG. 3 shows results of flow cytometry analysis of the expression of pluripotent stem cell markers in cells from spherical spheroids produced by rotary-culturing with an RWV bioreactor for 3 days. A: FSC-A/SSC-A dot plot; B: SSC-A/PI dot plot; C: SSEA-4/TRA-1-60 dot plot. D shows the number of events and proportion thereof in each of regions defined in FIGS. 3A, 3B, and 3C.
Figure 4:
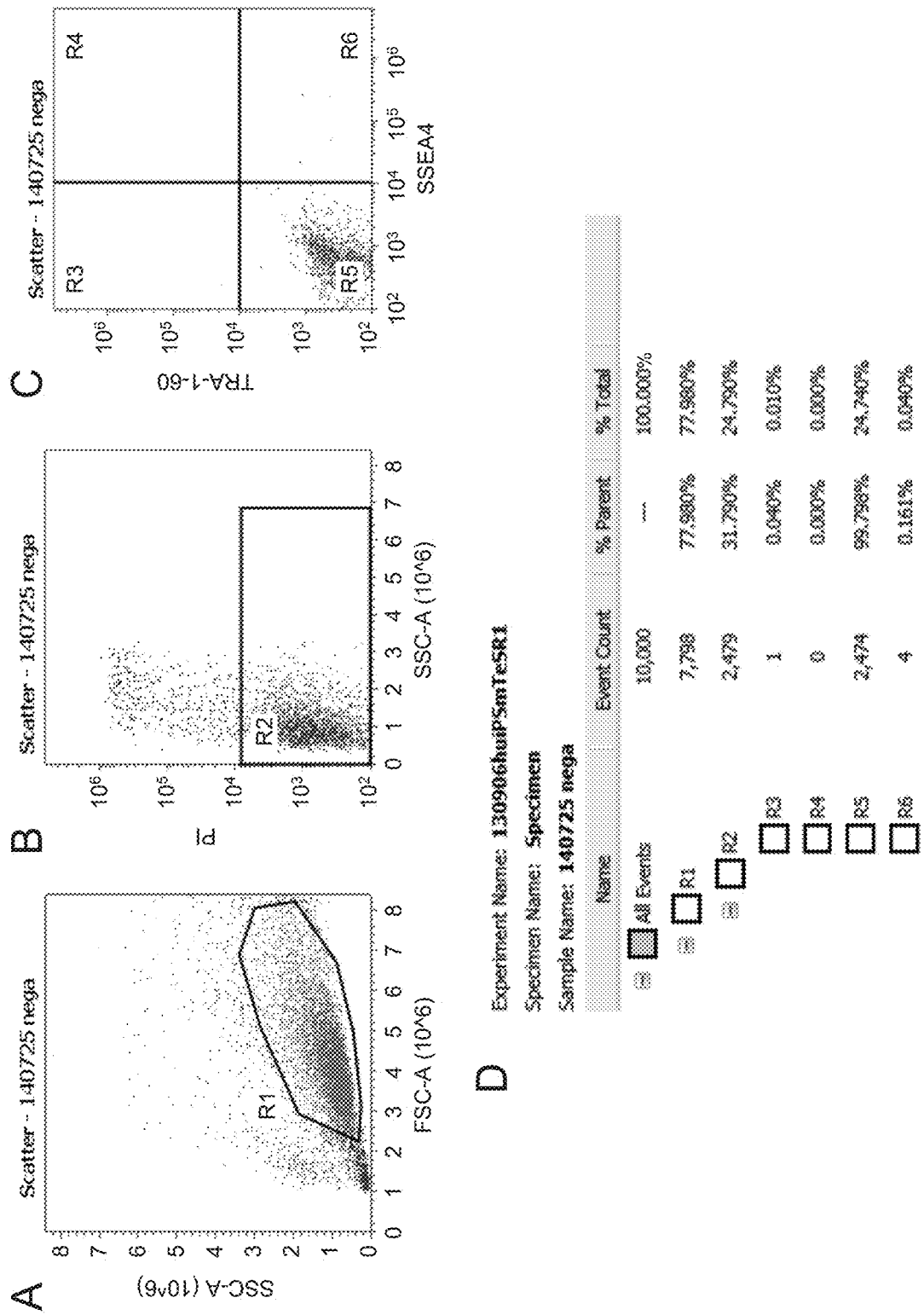
FIG. 4 shows results of flow cytometry analysis of a negative control. A: FSC-A/SSC-A dot plot; B: SSC-A/PI dot plot; C: SSEA-4TRA-1-60 dot plot. D shows the number of events and proportion thereof in each of regions defined in FIGS. 4A, 4B, and 4C.

The results are shown in FIG. 3 (test sample) and FIG. 4 (negative control). The markers SSEA-4 and TRA-1-60 were both positive (FIG. 3), which indicates that the 253G1 cells cultured with an RWV bioreactor are maintained in an undifferentiated state as iPS cells.

[Example 3] Evaluation of Expression of iPS Cell-Marker Genes by Real-Time PCR

To evaluate the expression levels of iPS cell-marker genes in 253G1 cells cultured with an RWV bioreactor, real-time PCR analysis was performed. The undifferentiation marker genes Nanog, Oct3/4 (Pou5fl), and Sox2 were targeted.

Real-time PCR analysis was performed by using a StepOne™ Real-Time PCR System (Life Technologies, Applied Biosystems) in accordance with the following procedure. First, the 253G1 cells detached with 5 mM EDTA were rotary-cultured in a 10 µM ROCK inhibitor Y27632-containing mTeSR1 medium with an RWV bioreactor for 3 days in the same manner as in Examples 1 and 2, and spheroids produced were collected, and the resulting cell pellets were frozen at −80° C. In parallel, the 253G1 cells detached with 5 mM EDTA were seeded on a culture dish coated with Matrigel, and cultured (two-dimensionally cultured) in an mTeSR1 medium for 3 days, and then centrifuged to collect the cells, and the resultant cell pellets were frozen at −80° C. The cell pellets cryopreserved at −80° C. were thawed on ice, and total RNA was extracted by using an RNeasy® Mini Kit (QIAGEN). The RNA concentration of the extracted total RNA sample was measured using the spectrophotometer, NanoDrop 1000 Spectrophotometer (Thermo Fischer Scientific Inc.). cDNA was synthesized from 1.5 µg of the total RNA in a reaction system of 20 µL using a High-Capacity RNA-to-cDNA Kit (Applied Biosystems). Subsequently, a TaqMan® Fast Universal PCR Master Mix (2×), No AmpErase UNG (Applied Biosystems), which was a premix solution for enzymatic reaction containing DNA polymerase, a substrate, and a buffer, etc., and an assay mix (TaqMan® Gene Expression Assays, Inventoried (Applied Biosystems)) containing ready-for-use primers and probe for real-time PCR measurement for each of the above target genes were mixed together to prepare a reaction mix. Among the TaqMan® Gene Expression Assays, a product of Assay ID: Hs04260366_g1 was used for the target undifferentiation marker gene Nanog, a product of Assay ID: Hs04260367_gH was used for the target undifferentiation marker gene Oct3/4 (Pou5fl), and a product of Assay ID: Hs01053049_s1 was used for the target unditferentiation marker gene Sox2. For GAPDH (glyceraldehyde-3-phosphate dehydrogenase) to be used as an endogenous control (reference gene), a product of Assay ID: Hs99999905_m1 was used.

Measurement of the quantity of RNA by real-time PCR was performed in accordance with the protocol of the manufacturer, and analysis was performed by the ΔΔCT method with Applied Biosystems StepOne™ Real-Time PCR System Software v2.2.2.

Figure 5:
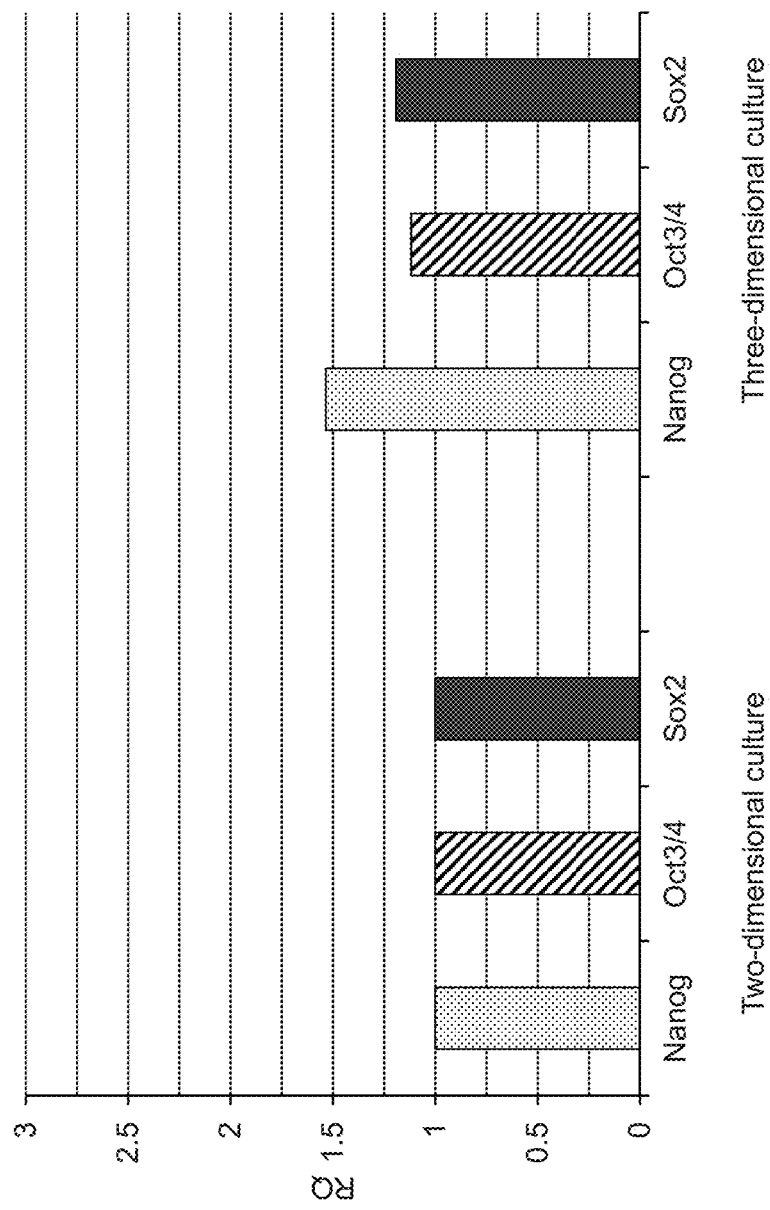
FIG. 5 is a graph for comparison of the expression levels of the undifferentiation marker genes Nanog, Oct3/4, and Sox2 between 253G1 cells from spherical spheroids produced by rotary-culturing with an RWV bioreactor for 3 days (three-dimensional culture) and two-dimensionally cultured 253G1 cells. Left: results for two-dimensional culture; and right: results for three-dimensional culture.

Spherical spheroids prepared by rotary culture of 253G1 cells with an RWV bioreactor for 3 days and 253G1 cells two-dimensionally cultured on Matrigel for 3 days in parallel were compared for the expression levels based on relative quantification by real-time PCR and the ΔΔCT method of the undifferentiation marker genes Nanog, Oct3/4, and Sox2. FIG. 5 shows the results. As is clear from FIG. 5, the spherical spheroids formed through rotary culture (three-dimensional culture) (FIG. 5, right) had a higher expression level for any of the three representative undifferentiation marker genes than in the case of conventional two-dimensional culture (FIG. 5, left). The same experiment was carried out a plurality of times, and similar results were obtained in all of the experiments. These demonstrate that rotary culture with an RWV bioreactor is superior to two-dimensional culture in that the rotary culture results in a higher maintenance in an undifferentiated state.

[Example 4] Experiment for Differentiation of iPS Cells from Spherical Spheroids Produced by Rotary Culture with RWV Bioreactor In accordance with the method described in Example 1, the 253G1 cells detached with 5 mM EDTA were seeded in a 10 mL vessel, and rotary-cultured in a 10 μM ROCK inhibitor Y27632-containing mTeSR1 medium with an RWV bioreactor for 3 days to produce spherical spheroids.

The resulting spheroids were subjected to observations of triploblastic differentiation by using the triploblastic differentiation kit, Stem Cell Kit: Human Pluripotent Stem Cell Functional Identification Kit (R&D Systems, Inc.). First, spheroids were dispersed into single cells using Accutase™, and the cells were seeded in an MEF-conditioned medium containing 4 ng/mL of FGF Basic in a 24-well dish coated with a Culture BME (Cultrex*PathClear*BME Reduced Growth factor Basement Membrane Extract, R&D Systems, Inc.) at a cell density of $1.1\times10^5$ cells/cm$^2$. The cells were cultured to reach 50% confluence, and then induction of differentiation was performed by using a differentiation-inducing medium which is an ectodermal, mesodermal, or endodermal differentiation medium. For induction of ectoderm differentiation, the medium was replaced with the Ectoderm Differentiation Media accompanying the above kit (day 1) and culture was performed while the medium was further replaced with the Ectoderm Differentiation Media in the same manner on day 2 and day 3, and thereafter fluorescent antibody staining was performed on day 4 with an antibody capable of detecting the expression of the ectoderm marker Otx2. For induction of mesoderm differentiation, the medium was replaced with the Mesoderm Differentiation Media accompanying the above kit (day 1) and culture was performed while the medium was further replaced with the Mesoderm Differentiation Media in the same manner after 12 to 16 hours, and fluorescent antibody staining was performed with an antibody capable of detecting the expression of the mesoderm marker Brachyury after 24 to 36 hours of the first medium replacement with the differentiation-inducing medium. For induction of endoderm differentiation, the medium was replaced with the Endoderm Differentiation Media I accompanying the above kit (day 1) and culture was performed while the medium was replaced with the Endoderm Differentiation Media II after 16 to 24 hours of the first medium replacement with the differentiation-inducing medium and the medium was further replaced with the Endoderm Differentiation Media II on day 3, and fluorescent antibody staining was performed with an antibody capable of detecting the expression of the endoderm marker Sox17 on day 4. Specifically, fixation and staining of cells were performed as follows: the 24-well dish after culturing was washed with PBS, and treated with 4% paraformaldehyde/PBS at room temperature for 20 minutes for fixation; and then the dish was washed with 1% BSA/PBS and blocked with a PBS solution containing 0.3% Triton X-100, 1% BSA, and 10% donkey serum. Then, the dish was incubated (at room temperature, for 3 hours) with a goat anti-human Otx2 antibody (for detection of the ectoderm marker), a goat anti-human Brachyury antibody (for detection of the mesoderm marker), or a goat anti-human SOX17 antibody (for detection of the endoderm marker) as a primary antibody, washed with 1% BSA/PBS, and then incubated with NL557-conjugated donkey anti-goat secondary antibody (R&D NL001) (1:200 dilution) added thereto, at room temperature for 60 minutes. After washing, a microscope slide of the cell sample was prepared, and observed with fluorescence microscope. For fluorescence measurement, photographing was performed at an identical light source intensity and an identical sensitivity. For a control, incubation was performed only with a buffer not containing an antibody as a primary antibody, and the same experiment was carried out.

Figure 6:
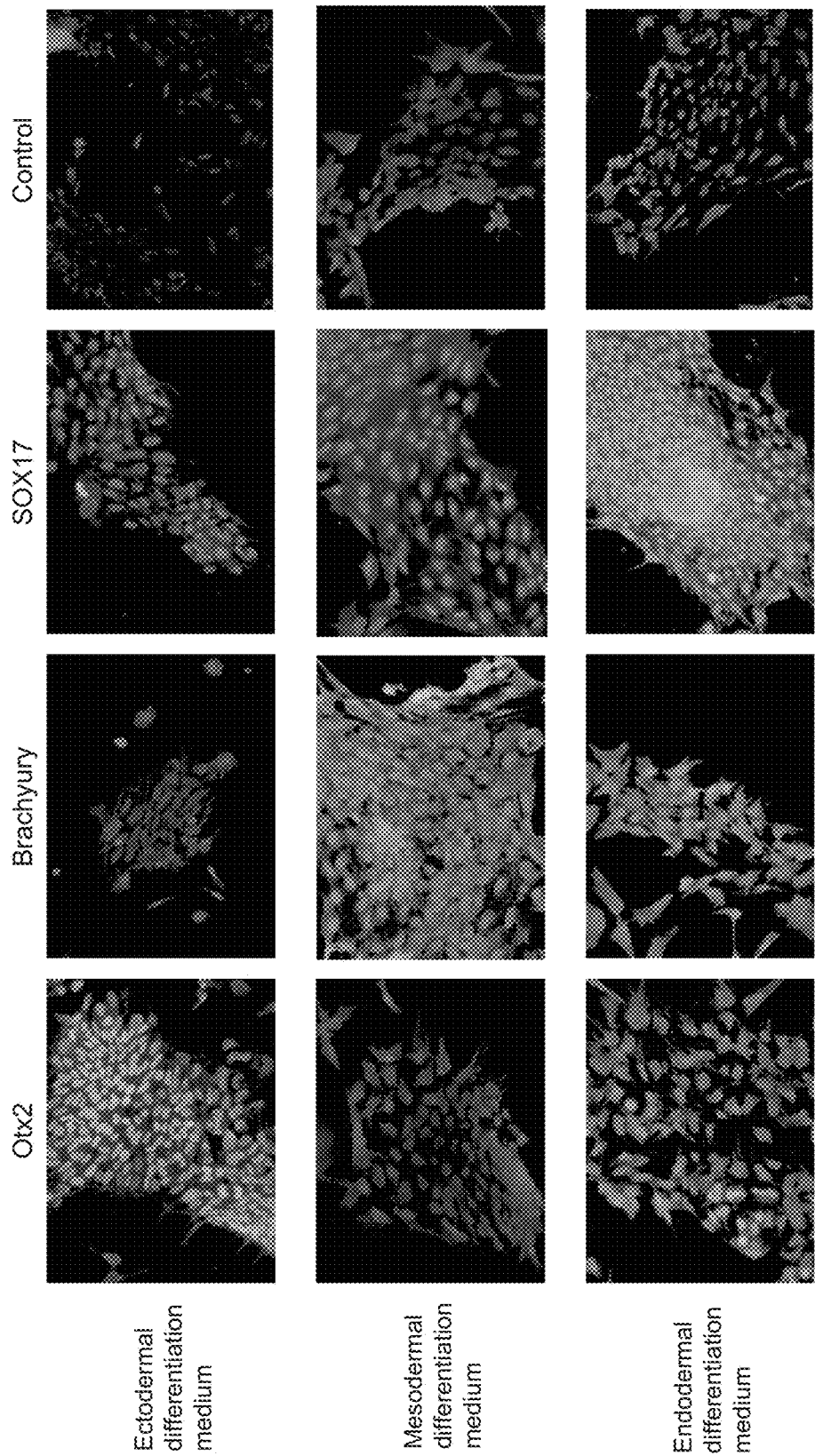
FIG. 6 shows results of staining of 253G1 cells from spherical spheroids produced by rotary-culturing with an RWV bioreactor for 3 days (three-dimensional culture) by using a triploblastic differentiation kit. An anti-Otx2 antibody (for ectodermal staining), an anti-Brachyury antibody (for mesodermal staining), and an anti-Sox17 antibody (for endodermal staining) were used for staining.

The results are shown in FIG. 6. From difference in fluorescence intensity, the expressions of Otx2, Brachyury, and SOX17 were shown in the cultures with the ectodermal differentiation medium, mesodermal differentiation medium, and endodermal differentiation medium, respectively (FIG. 6). These results indicate that iPS cells constituting spherical spheroids obtained by rotary culture with an RWV bioreactor retain the capacity to differentiate into ectoderm, mesoderm, and endoderm, after dispersion.

[Example 5] Experiment of Proliferation of iPS Cells by RWV Bioreactor with 50 mL Vessel In accordance with the method described in Example 1 (1), the 25301 cells detached with 5 mM EDTA into small spheroids were seeded in a 50 mL vessel, and rotary-cultured in a 10 μM ROCK inhibitor Y27632-containing mTeSR1 medium with an RWV bioreactor at a rotation rate of 8 rpm for 3 days to produce spherical spheroids. Suitable seeding density of the cells was investigated in accordance with the method described in Example 1 (3). As a result, the cells seeded at $2.5\times10^6$ cells in total in the 50 mL vessel showed the most highest proliferation rate, and in other word, the seeding density ($5.0\times10^4$ cells/cm$^3$) comparable to that shown for 10 mL vessel above provided a particularly high proliferation rate. The proliferation rate was 3.8- to 4.5-fold in 3 days.

[Example 6] Serial Subculture Test

Figure 7:
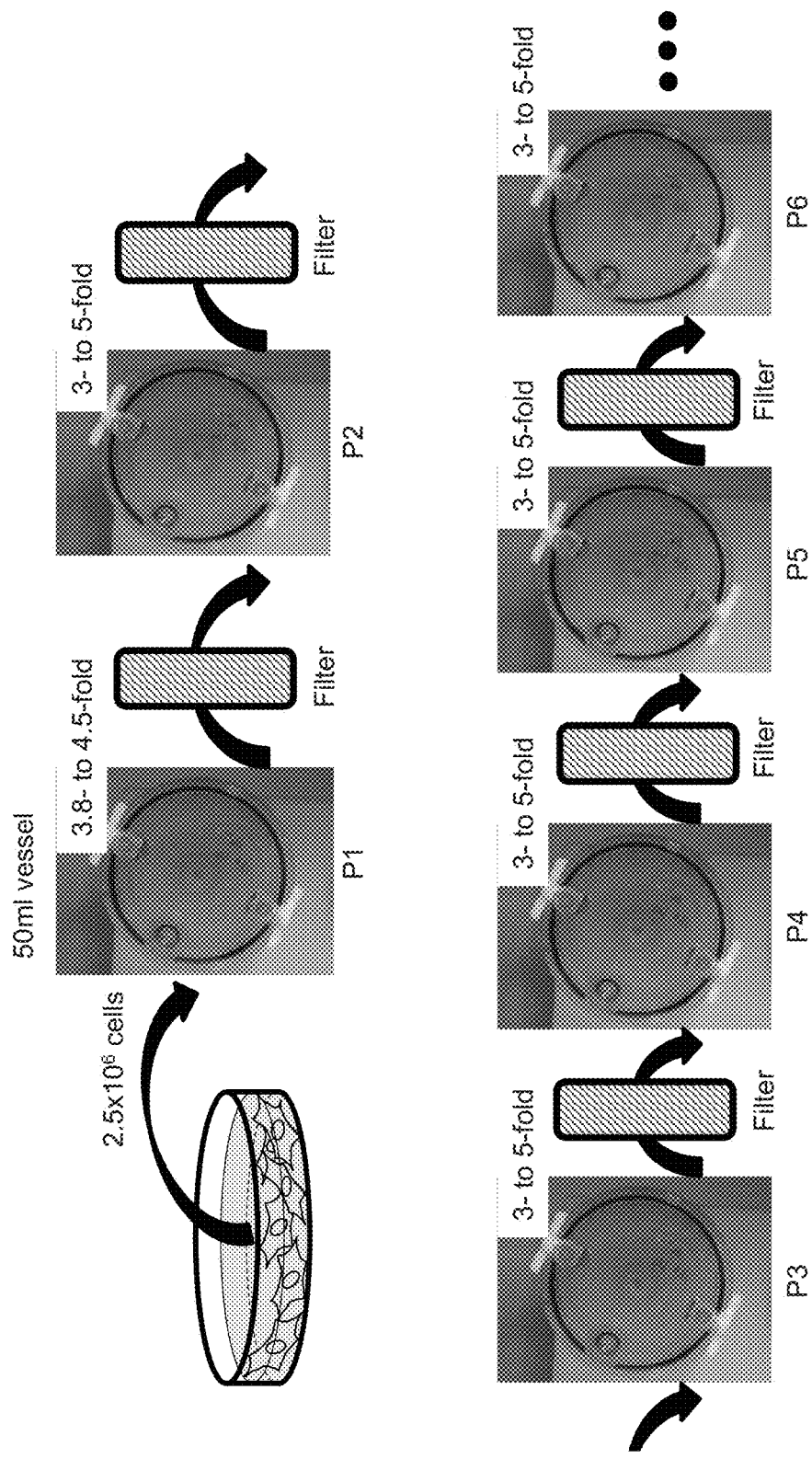
FIG. 7 is a schematic illustrating a serial subculture test for 253G1 cells with a 50 mL vessel.

In this Example, a serial subculture test was carried out. FIG. 7 schematically illustrates the procedures.

In accordance with the method described in Example 5, the 253G1 cells ($2.5\times10^6$ cells) detached with 5 mM EDTA into small spheroids were seeded in a 50 mL vessel, and rotary-cultured in a 10 μM ROCK inhibitor Y27632-containing mTeSR1 medium with an RWV bioreactor for 3 days to produce spherical spheroids.

Subsequently, the spherical spheroids were collected from the 50 mL vessel with a pipette, and the spherical spheroids were disrupted into small spheroids by passing the spherical spheroids through a filter having a filter mesh size of 70 μm (BD Falcon® 70 μm Cell Strainer Nylon REF 352350; BD Biosciences) under a pipetting pressure. The resulting small spheroids (small spheroids obtained through mechanical disrupting) were seeded in a fresh 50 mL vessel and rotary-cultured at 8 rpm for 3 days to produce spherical spheroids. Thereafter, disrupting through a 70 μm filter, seeding in a fresh 50 mL vessel, and rotary culture for 3 days were repeated (serial subculture).

Figure 8:
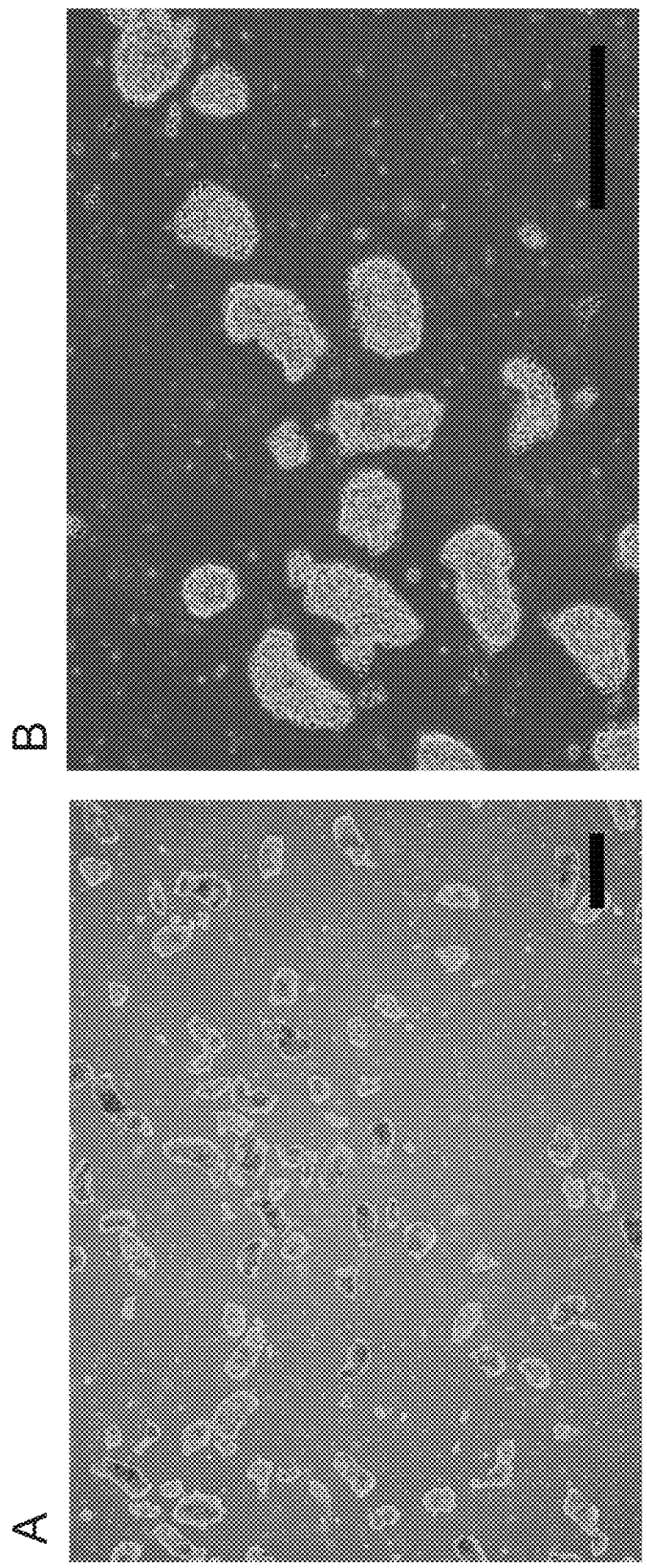
FIG. 8 shows photographs of phase contrast images of small spheroids prepared by disrupting spherical spheroids produced by culturing 253G1 cells with a 50 mL vessel for 3 days via passing them through a 70 μm filter. A: phase contrast image at a low magnification, in which the bar indicates 1000 μm; and B: phase contrast image at a high magnification, in which the bar indicates 500 μm.

FIG. 8 shows images of the small spheroids immediately after disrupting through a 70 μm filter. FIG. 8A shows a phase contrast image at a low magnification, and FIG. 8B shows a phase contrast image at a high magnification. The small spheroids after disrupting via a filter were in an elongated shape and had a size (approximately 30 to 200 cells per small spheroid) with a minor axis of 70 to 100 μm and a major axis of 70 to 400 µm, and thus were clearly small spheroids in a morphological sense. The small spheroids were seeded in a fresh vessel, and rotary-cultured for 3 days to prepare larger spherical spheroids.

The above-described subculture was repeatedly performed nine times (P9; total culturing period: 30 days), and a similar proliferation rate of 3- to 5-fold was constantly observed (FIG. 7).

[Example 7] Evaluation on Maintenance of Undifferentiated State Via Serial Subculture To evaluate the expression levels of iPS cell-marker genes in 253G1 cells subjected to serial subculture using an RWV bioreactor with an 50 mL vessel, a portion of spherical spheroids after each rotary culture (three-dimensional culture; P5 to P8) and before filtering was collected respectively, and subjected to real-time PCR analysis. The undifferentiation marker genes Nanog, Oct3/4 (Pou5fl), and Sox2 were targeted for the analysis. The experiment procedures of real-time PCR are identical to those in Example 3.

Figure 9:
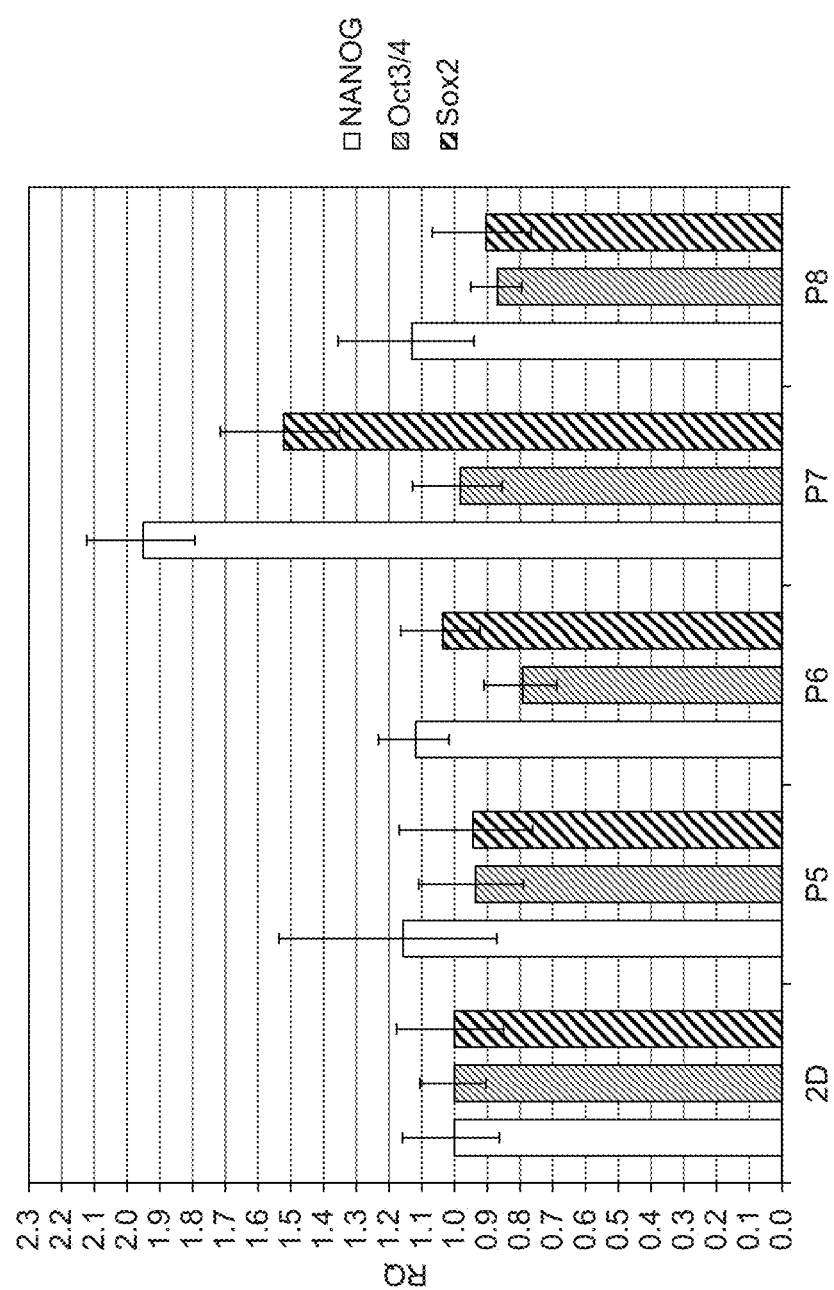
FIG. 9 shows results of real-time PCR measurement of the expression levels of undifferentiation markers in spherical spheroids collected after serial culture of 253G1 cells in a 50 mL vessel. The expression levels of the undifferentiation marker genes Nanog, Oct3/4, and Sox2 were compared with the expression levels in two-dimensionally cultured 253G1 cells. 2D: results obtained for two-dimensional culture. P5, P6, P7, and P8: results obtained after respective subcultures from dish culture (see also, the schematic in FIG. 7).

The results are shown in FIG. 9. No significant reduction was observed for the expression level of any of Nanog, Oct3/4, and Sox2, which indicates that an undifferentiated state was maintained till P9, which was comparable to that for two-dimensional culture.

A proliferation rate of 3- to 5-fold was obtained in each culture stage, and thus it follows that $10^{10}$ or more iPS cells that are maintained in an undifferentiated state can be theoretically obtained when starting with $2.5 \times 10^6$ cells by repeating serial culture using the whole amount of cultured cells until P9. This indicates that the method according to the present invention enables mass culture of iPS cells while maintaining the cells in the undifferentiated state.

[Example 8] Differentiation Induction Test

In accordance with the method described in Example 5, the 253G cells were rotary-cultured in a 10 µM ROCK inhibitor Y27632-containing mTeSR1 medium using an RWV bioreactor with a 50 mL vessel at 37° C. at a rotation rate of 8 rpm for 3 days to produce spherical spheroids (iPS spheroids). Thereafter, the mTeSR1 medium was completely replaced with a neuronal differentiation medium (STEMdiff™ Neural Induction Medium, STEMCELL Technologies Inc., cat #05835) (day 0), and culture was continued under the same conditions. Subsequent medium replacements were performed on day 3, day 5, day 7, and day 10, and rotary culture was performed until day 12. Evaluation on differentiation of the cells constituting the iPS spheroids into nerve cells was performed by an immune antibody staining method and real-time PCR method.

In the immune antibody staining method, the iPS spheroids were dispersed into cells with Accutase™ (Innovative Cell Technologies, Inc.), and the cells were seeded on a 3 cm dish and cultured in a neuronal differentiation medium for 20 hours, and immunostained in accordance with the universal protocol (ABC method). For immunostaining, an anti-Pax6 antibody (BioLegend Inc., rabbit polyclonal anti-Pax-6 antibody) as an indicator of nerve cells and an anti-Oct3/4 antibody (hES/iPS Cell Characterization Kit, Applied StemCell, Inc., cat # ASK-3006) as an indicator of undifferentiated iPS cells were used.

Evaluation by the real-time PCR method was performed in accordance with an analysis method using the ΔΔCT method, as in Example 3. Nanog was used for an undifferentiation marker of iPS cells. For a primer/probe set, a Taqman Gene Expression assay (ID: Hs04260366_g1) was used. Specifically, Pax6 and Sox1 were selected as neuronal differentiation markers, for which products of IDs: Hs00240871_m1 and Hs01057642_s1 of the Taqman Gene Expression assays were used, respectively. For a primer/probe set for GAPDH (glyceraldehyde-3-phosphate dehydrogenase) to be used as the endogenous control (reference gene), a product of Assay ID: Hs99999905_m1 was used.

Figure 10:
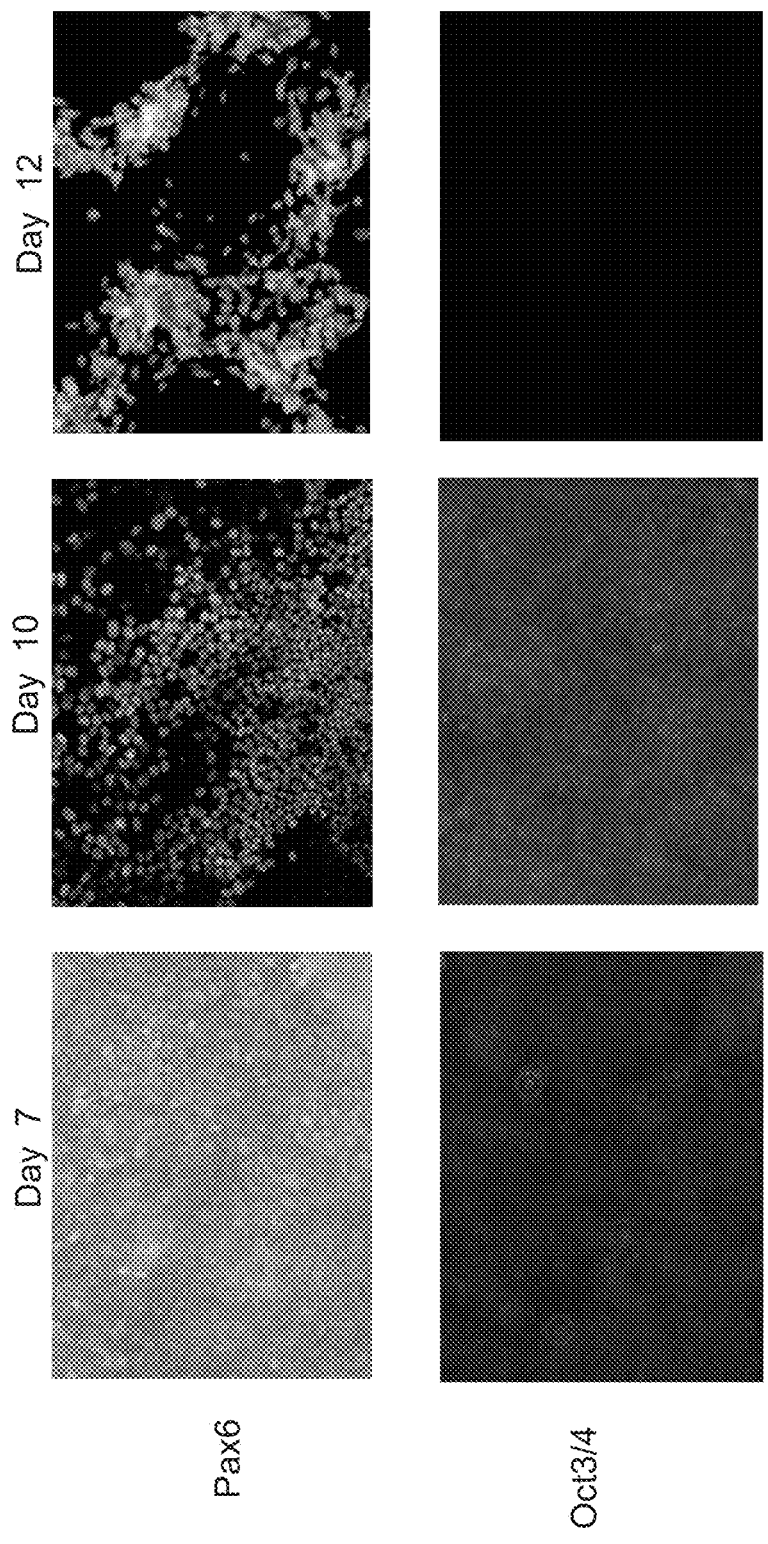
FIG. 10 shows results of immune antibody staining targeting the neuronal differentiation marker Pax6 (top) and the undifferentiation marker Oct3/4 (bottom) for cells of spheroids cultured in a neuronal differentiation medium after rotary-culturing with an RWV bioreactor.

FIG. 10 shows the results of immune antibody staining. As shown in FIG. 10, immunostaining results with an anti-Pax6 antibody and anti-Oct3/4 antibody on day 7, day 10, and day 12 (day 0: the starting day of culture in a neuronal differentiation medium) were compared. Although little staining due to an anti-Oct3/4 antibody was observed on any of day 7, day 10, and day 12, weak staining due to an anti-Pax6 antibody was observed on day 7, and for subsequent day 10 and day 12, the intensity increased over time. From comparison between the result of staining on day 12 and a result of nuclear staining with DAPI, almost 90% of the cells were found to be positive for staining with an anti-Pax6 antibody.

Figure 11:
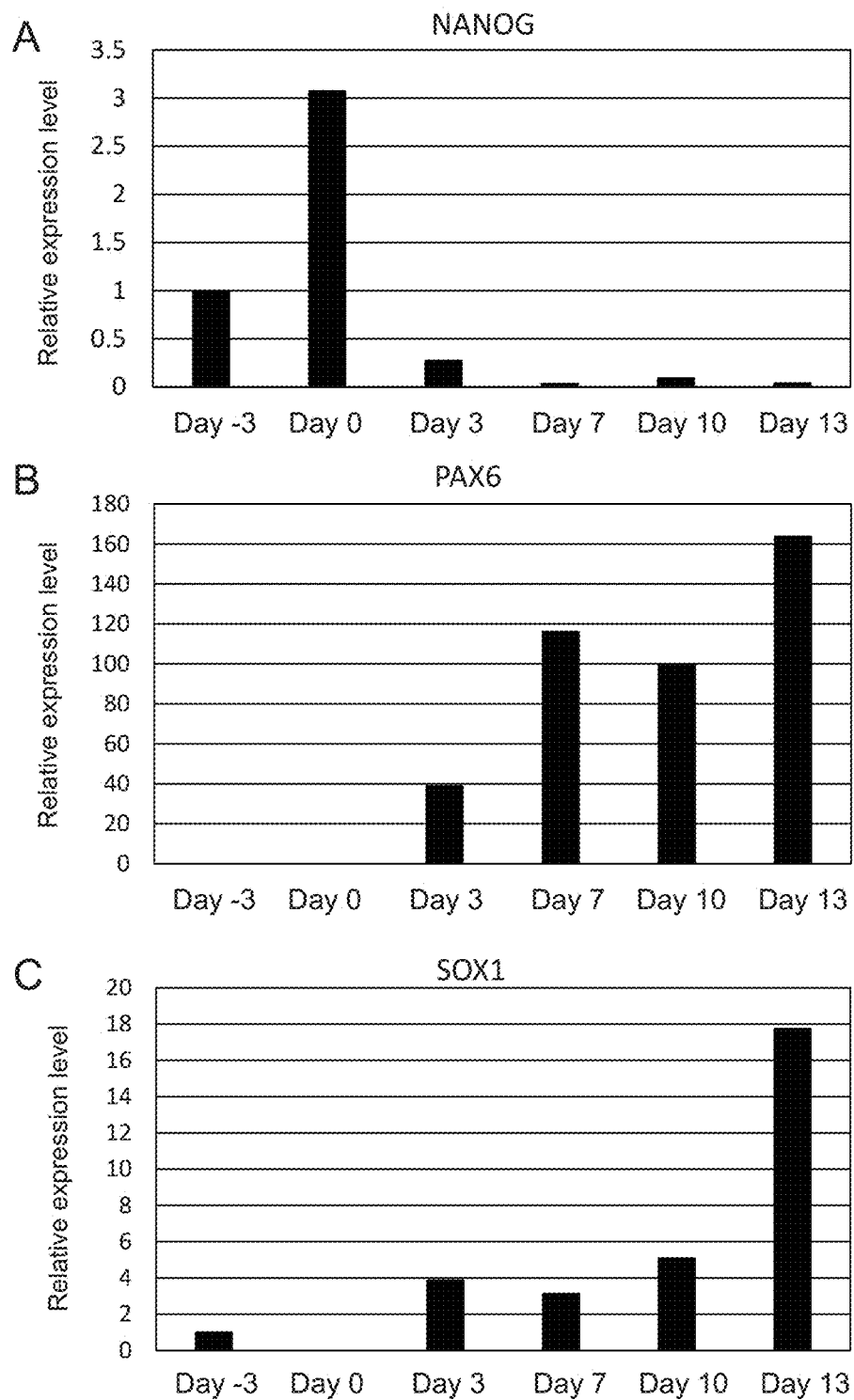
FIG. 11 shows results of real-time PCR analysis for cells of spheroids cultured in a neuronal differentiation medium after rotary-culturing with an RWV bioreactor. A, B, and C show culturing time-dependent transition of the expression level of Nanog, Pax6, and Sox1, respectively.

The results of real-time PCR analysis are shown in FIG. 11. Therein, the expression levels of Nanog (FIG. 11A), Pax6 (FIG. 11B), and Sox1 (FIG. 11C) on day −3 (3 days before seeding of cells in an RWV vessel), day 0 when first medium replacement with a neuronal differentiation medium was performed, and day 3, day 7, day 10, and day 13 are shown. The expression level of Nanog, an undifferentiation marker of iPS cells, increased by approximately 3-fold, after seeding in an RWV vessel, through culture in a medium for maintaining an undifferentiated state (mTeSR1) for 3 days (day 0); and the expression level decreased to a level of approximately 1/10 of that on day 0, after 3 days of medium replacement with a neuronal differentiation medium; and on or after day 7 the expression level decreased by approximately two orders of magnitude compared with that on day 0. On the other hand, the expression of Pax6, a neuronal differentiation marker, was not found during the period of culturing in a medium for maintaining an undifferentiated state (from day −3 to day 0), and drastically increased in 3 days after medium replacement with a neuronal differentiation medium, and an increasing tendency was observed till day 13. For Sox1, one neuronal differentiation marker, the expression was found only to slight extent during the period of culturing in a medium for maintaining an undifferentiated state, and in contrast the expression level increased after 3 days of medium replacement with a neuronal differentiation medium and increase of the expression level was found till day 13, similarly to the case of Pax6.

These results indicate that the cells in the iPS spheroids differentiated into nerve cells via culture in a neuronal differentiation medium. This demonstrates that, after constructing iPS spheroids by culturing iPS cells in a medium for maintaining an undifferentiated state with an RWV bioreactor in a pseudo-microgravity environment, simply culturing the cells of the iPS spheroids in a neuronal differentiation medium replaced for the medium can bring the iPS cells constituting the iPS spheroids out of an undifferentiated state while the form of the spheroids is kept and induce them to differentiate into nerve cells.

INDUSTRIAL APPLICABILITY

The present invention can be used to proliferate pluripotent stem cells such as induced pluripotent stem cells and to efficiently produce spheroids. The method according to the present invention can be used for mass culture of pluripotent stem cells in a safer and more stable manner without any use of a feeder cell or a coating material while maintaining the pluripotent stem cells in an undifferentiated state. In addition, the present invention can be used for mass production of cells differentiated from pluripotent stem cells.

All of the publications, patents, and patent applications cited herein are to be directly incorporated herein by reference.

We claim:

1. A method for culturing induced pluripotent stem cells (iPS cells), the method comprising:
   a) culturing isolated iPS cells that are seeded in a culture medium at a cell density of $4\times10^4$ to $6\times10^4$ cells/cm$^3$ in a pseudo-microgravity environment to proliferate the iPS cells while maintaining the iPS cells in an undifferentiated state, thereby forming and growing spheroids of the iPS cells;
   b) performing one cycle of disrupting the resulting spheroids by passing the spheroids through a filter having a filter mesh size of 40 to 100 μm to generate disrupted spheroids; and
   c) further culturing the disrupted spheroids in the pseudo-microgravity environment, thereby forming and growing spheroids, or repeating the cycle two or more times, wherein the culturing in step a) and c) is performed in the presence of a Rho-associated kinase (ROCK) inhibitor,
wherein the pseudo-microgravity environment is an environment in which an object is subjected to a gravity corresponding to $1/10$ to $1/100$ of the earth's gravity in time average, and the pseudo-microgravity environment is obtainable by using a uniaxial rotary bioreactor capable of achieving a pseudo-microgravity environment on earth by canceling out the earth's gravity with stresses caused by rotation, and wherein a culture container having a volume of 5 mL to 100 mL and a rotation speed of 6 to 8.5 rpm are used for culturing the pluripotent stem cells in the pseudo-microgravity environment in step a) and c).

2. The method according to claim 1, wherein the culturing is performed in the absence of a cell scaffold material.

3. The method according to claim 1, wherein the uniaxial rotary bioreactor is a Rotating Wall Vessel (RWV) bioreactor.

4. The method according to claim 1, wherein the disrupted spheroids are cultured in the pseudo-microgravity environment for 2 to 7 days to form and grow spheroids.

5. A method for inducing differentiation of iPS cells, the method comprising culturing iPS cells by the method according to claim 1, and further culturing the iPS cells in a differentiation-inducing medium.

6. The method according to claim 5, wherein the culturing in the differentiation-inducing medium is performed in a pseudo-microgravity environment.

7. The method according to claim 1, wherein the spheroids have a diameter of 300 μm to 1000 μm.

8. The method according to claim 5, wherein the iPS cells to be further cultured are spheroids of iPS cells.

* * * * *